US010688284B2

(12) United States Patent
Hill et al.

(10) Patent No.: US 10,688,284 B2
(45) Date of Patent: Jun. 23, 2020

(54) STEERING TECHNIQUES FOR SURGICAL INSTRUMENTS

(71) Applicants: Massachusetts Institute of Technology, Cambridge, MA (US); The General Hospital Corporation, Boston, MA (US)

(72) Inventors: Westin Michael Hill, Cambridge, MA (US); Matthew Roy Johnson, Somerville, MA (US); Tara Lee Schmidt Boettcher, Chelmsford, MA (US); Patrick James Codd, Boston, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 378 days.

(21) Appl. No.: 14/550,436

(22) Filed: Nov. 21, 2014

(65) Prior Publication Data
US 2015/0148602 A1   May 28, 2015

Related U.S. Application Data

(60) Provisional application No. 61/907,812, filed on Nov. 22, 2013, provisional application No. 62/057,415, filed on Sep. 30, 2014.

(51) Int. Cl.
*A61B 1/00* (2006.01)
*A61B 1/06* (2006.01)
(Continued)

(52) U.S. Cl.
CPC ....... *A61M 25/0147* (2013.01); *A61B 1/0055* (2013.01); *A61B 1/00154* (2013.01);
(Continued)

(58) Field of Classification Search
CPC .......... A61M 25/0147; A61M 25/0133; A61M 25/0152; A61M 25/0136; A61M 25/0141;
(Continued)

(56) References Cited

U.S. PATENT DOCUMENTS 3,908,663 A   9/1975   Viek
5,318,528 A   6/1994   Heaven et al.
(Continued)

FOREIGN PATENT DOCUMENTS

WO   WO-2007059233   5/2007
WO   WO-2009090161   7/2009
(Continued)

OTHER PUBLICATIONS

ISA, "PCT Application No. PCT/US15/53358 International Search Report and Written Opinion dated Jun. 6, 2016", 14 pages.
(Continued)

*Primary Examiner* — Alexandra L Newton
*Assistant Examiner* — Genja M Frankert
(74) *Attorney, Agent, or Firm* — Strategi Patents, P.C.

(57) ABSTRACT

A steerable endoscopic tool uses concentric sleeves of varying curvature to steer a tool tip toward or in the direction of a location of surgical interest. By rotating and/or axially displacing such sleeves relative to one another the tool tip may be maneuvered within a current field of view with several degrees of freedom without any physical movement of an endoscope, thus facilitating improved surgical access and control without complex mechanical systems in the endoscope or at the surgical site.

21 Claims, 9 Drawing Sheets

(51) Int. Cl.
*A61B 1/04* (2006.01)
*A61M 25/01* (2006.01)
*A61B 18/24* (2006.01)
*A61B 1/018* (2006.01)
*A61B 1/005* (2006.01)
*A61B 18/20* (2006.01)
*A61B 18/22* (2006.01)
*A61B 18/00* (2006.01)
*A61B 17/00* (2006.01)
*A61M 25/06* (2006.01)

(52) U.S. Cl.
CPC ......... *A61B 1/018* (2013.01); *A61M 25/0133* (2013.01); *A61B 2017/00331* (2013.01); *A61B 2018/00029* (2013.01); *A61B 2018/00339* (2013.01); *A61B 2018/00577* (2013.01); *A61B 2018/00982* (2013.01); *A61B 2018/20361* (2017.05); *A61B 2018/2238* (2013.01); *A61B 2218/002* (2013.01); *A61M 25/0136* (2013.01); *A61M 25/0141* (2013.01); *A61M 25/0152* (2013.01); *A61M 2025/015* (2013.01); *A61M 2025/0681* (2013.01); *A61M 2205/0266* (2013.01)

(58) Field of Classification Search
CPC .......... A61M 2025/0681; A61B 18/22; A61B 1/018; A61B 1/0055; A61B 1/00154; A61B 2017/00331; A61B 2018/00029; A61B 2018/00339; A61B 2018/0577
See application file for complete search history.

(56) References Cited

U.S. PATENT DOCUMENTS

| | | | |
|---|---|---|---|
| 5,607,435 A | 3/1997 | Sachdeva et al. | |
| 5,707,368 A | 1/1998 | Cozean et al. | |
| 5,921,915 A | 7/1999 | Aznoian et al. | |
| 6,572,593 B1 | 6/2003 | Daum et al. | |
| 7,914,517 B2 | 3/2011 | Baran et al. | |
| 7,963,912 B2 | 6/2011 | Zwolinski et al. | |
| 8,079,364 B2* | 12/2011 | Lowe | A61F 6/18 128/830 |
| 9,155,452 B2 | 10/2015 | Rothe et al. | |
| 9,192,287 B2 | 11/2015 | Peh et al. | |
| 2002/0068868 A1 | 6/2002 | Thompson et al. | |
| 2004/0082969 A1 | 4/2004 | Kerr | |
| 2005/0020901 A1 | 1/2005 | Belson et al. | |
| 2005/0288622 A1 | 12/2005 | Albrecht et al. | |
| 2007/0249989 A1 | 10/2007 | Longo et al. | |
| 2008/0015569 A1 | 1/2008 | Saadat et al. | |
| 2008/0021274 A1 | 1/2008 | Bayer et al. | |
| 2008/0091170 A1 | 4/2008 | Vargas et al. | |
| 2008/0195081 A1 | 8/2008 | Moll et al. | |
| 2008/0215067 A1 | 9/2008 | Dupont et al. | |
| 2009/0024141 A1* | 1/2009 | Stahler | A61B 34/71 606/130 |
| 2009/0124858 A1 | 5/2009 | Oskin et al. | |
| 2009/0138025 A1 | 5/2009 | Stahler et al. | |
| 2009/0157060 A1* | 6/2009 | Teague | A61B 17/221 606/1 |
| 2009/0248045 A1* | 10/2009 | Trovato | A61B 17/3421 606/130 |
| 2010/0022824 A1 | 1/2010 | Cybulski et al. | |
| 2010/0081877 A1 | 4/2010 | Vakharia | |
| 2011/0071544 A1 | 3/2011 | Steger et al. | |
| 2011/0092810 A1 | 4/2011 | Trovato et al. | |
| 2011/0112363 A1 | 5/2011 | Koga et al. | |
| 2011/0251455 A1* | 10/2011 | Popovic | A61B 17/3421 600/104 |
| 2011/0282152 A1 | 11/2011 | Cant | |
| 2011/0288572 A1 | 11/2011 | Martin | |
| 2012/0215088 A1 | 8/2012 | Wang et al. | |
| 2012/0289816 A1 | 11/2012 | Mark et al. | |
| 2012/0316394 A1 | 12/2012 | Yoshida et al. | |
| 2013/0018303 A1* | 1/2013 | Webster | A61B 17/3417 604/95.01 |
| 2013/0102843 A1 | 4/2013 | Feuer et al. | |
| 2013/0144186 A1* | 6/2013 | Furlong | A61B 1/018 600/563 |
| 2013/0150831 A1* | 6/2013 | Griffiths | A61B 17/00 606/1 |
| 2013/0217970 A1 | 8/2013 | Weisenburgh, II et al. | |
| 2013/0225934 A1 | 8/2013 | Raybin et al. | |
| 2013/0267778 A1 | 10/2013 | Rehe | |
| 2014/0094659 A1 | 4/2014 | Hamazaki et al. | |
| 2014/0188127 A1 | 7/2014 | Dubrul et al. | |
| 2014/0228875 A1 | 8/2014 | Saadat | |
| 2014/0235943 A1 | 8/2014 | Paris et al. | |
| 2014/0276925 A1 | 9/2014 | Alves et al. | |
| 2015/0032117 A1* | 1/2015 | Kim | A61B 17/3415 606/108 |
| 2015/0035968 A1 | 2/2015 | Konomura et al. | |
| 2015/0080907 A1 | 3/2015 | Herrell et al. | |
| 2015/0366440 A1 | 12/2015 | Rothe et al. | |
| 2016/0038133 A1 | 2/2016 | Smith et al. | |
| 2016/0073859 A1 | 3/2016 | Kogiso et al. | |
| 2016/0095505 A1 | 4/2016 | Johnson et al. | |
| 2016/0287063 A1 | 10/2016 | Ramanujam et al. | |
| 2018/0256015 A1 | 9/2018 | Johnson et al. | |

FOREIGN PATENT DOCUMENTS

| | | |
|---|---|---|
| WO | WO-2015077584 | 5/2015 |
| WO | WO-2018183643 | 10/2018 |

OTHER PUBLICATIONS

Hendrick, R. J., et al., "A Multi-Arm Hand-Held Robotic System for Transurethral Laser Prostate Surgery," IEEE International Conference on Robotics and Automation, 2014, pp. 2850-2855.

Hendrick, R. J., et al., "Concentric Tube Robots for Transurethral Prostate Surgery: Matching the Workspace to the Endoscopic Field of View" Symposium on Medical Robotics; Department of Mechanical Engineering, Vanderbilt University, 2014, 2 pages.

Herrell, S. Duke., et al., "Future robotic platforms in urologic surgery: recent developments," www.co-urology.com; vol. 24 No. 1, Jan. 2014, pp. 118-126.

U.S. International Search Authority, "International Application Serial No. PCT/US14/66861, Search Report and Written Opinion dated May 22, 2015", 8 pages.

Yoon, Hyun-Soo et al., "Active Bending Endoscope Robot System for Navigation through Sinus Area", 2011 IEEE/RSJ International Conference on Intelligent Robots and Systems, Sep. 25-30, 2011, 6 pages.

Yoon, Hyun-Soo et al., "Error Compensation for a 2 DOF Bendable Endoscope Mechanism", 2013 13th International Conference on Control, Automation and Systems (ICCAS 2013) Oct. 20-23, 2013 in Kimdaejung Convention Center, Gwangju, Korea, Oct. 2013, 4 pages.

R. Cernat, et al., "Ex-vivo Endoscopic Laryngeal Cancer Imaging using two Forward-looking Fiber Optic Scanning Endoscope Probes", Progress in Biomedical Optics and Imaging—Proceedings of SPIE, vol. 8213, 2012, Article No. 82133M, Jan. 2012, 6 pages.

Makishi, Wataru et al., "Active Bending Electric Endoscope Using Shape Memory Alloy Coil Actuators", Proceedings of the First IEEE/RAS-EMBS International Conference on Biomedical Robotics and Biomechatronics, Article No. 1639088, Feb. 2006, pp. 217-219.

Maeda, Shigeo et al., "Active Endoscope With SMA (Shape Memory Alloy) Coil Springs", Proceedings of the IEEE Micro Electro Mechanical Systems (MEMS), Feb. 1996, pp. 290-295.

Iro, H. et al., "A new device for frontal sinus endoscopy: First clinical report", Otolaryngology—Head and Neck Surgery, vol. 125, Issue 6 Dec. 2001, pp. 613-616.

Arora, Aman et al., "Shape Memory Alloy Actuated Arm for Traversing Complex Trajectories", ICECT 2011—2011 3rd International Conference on Electronics Computer Technology, vol. 2, Apr. 2011, pp. 398-403.

(56) References Cited

OTHER PUBLICATIONS

Chandler, John E. et al., "Evaluation of a novel, ultrathin, tip-bending endoscope in a synthetic force-sensing pancreas with comparison to medical guide wires", Dove Press journal: Medical Devices: Evidence and Research, Dec. 22, 2011 , 12 pages.
Haga, Yoichi et al., "Microsystems for Minimally Invasive Medicine and Healthcare", ICEP 2014 Proceedings, 2014 , 4 pages.
Makishi, W. et al., "Development of active bending electric endoscope using shape memory alloy for disposable and thin endoscope", IEEJ Transactions on Sensors and Micromachines, vol. 131, Issue 3 2011 , pp. 102-110.
Venugopalan, V., "Pulsed Laser Abalation of Tissue: Surface Vaporization or Thermal Explosion", May 22, 1995 , pp. 184-189.
Ruetten, S. et al., "Endoscopic surgery of the lumbar epidural space (epiduroscopy): results of therapeutic intervention in 93 patients", Minim Invas Neurosurg 2003; 46: 1-4 Georg Thieme Verlag Stuttgart—New York—ISSN 0946-7211, 2003, 4 Pages.
WIPO, "International Application Serial No. PCT/US14/66861, International Preliminary Report on Patentability dated Jun. 2, 2016", 6 pages.
USPTO, "U.S. Appl. No. 14/872,006 Non-Final Office Action dated Dec. 12, 2017", 24 pages.
Johnson, Matt R. et al., "Ablation of Porcine Ligamentum Flavum With Ho:YAG, Q-Switched Ho:YAG, and Quadrupled Nd:YAG Lasers", Lasers in Surgery and Medicine 47:839-851 (2015) Sep. 2015 , pp. 839-851.
ISA, "PCT Application No. PCT/US18/25090 International Search Report and Written Opinion dated Jul. 6, 2018", 15 pages.
MIT, "Tools and Adaptations to Enable Endoscopic Spinal Surgery", http://technology.mit.edu/technologies/17646_tools-and-adaptations-to-enable-endoscopic-spinal-surgery , 3 Pages Total.
EPO, "EP Application Serial No. 15859643.7 Supplemental Search Report dated May 3, 2018", 6 pages.
Hogan, Hank "The Growing Role of Lasers in Treatments for Better Blood Flow", BioPhotonics https://www.photonics.com/Article.aspx?AID=64303, Mar. 2019, 4 Pages.
Wikipedia, "Living Hinge", https://en.wikipedia.org/wiki/Living_hinge, Apr. 21, 2019, 1 Page.
USPTO, "U.S. Appl. No. 15/978,976 Final Office Action dated Aug. 15, 2019", 26 pages.
USPTO, "U.S. Appl. No. 15/978,976 Non-Final Office Action dated Apr. 26, 2019", 20 pages.
EPO, "EP Application Serial No. 15859643.7 Communication Pursuant to Article 94(3) EPC dated Apr. 30, 2019", 4 pages.
WIPO, "PCT Application No. PCT/US18/25090 International Preliminary Report on Patentability dated Oct. 10, 2019", 10 pages.

\* cited by examiner

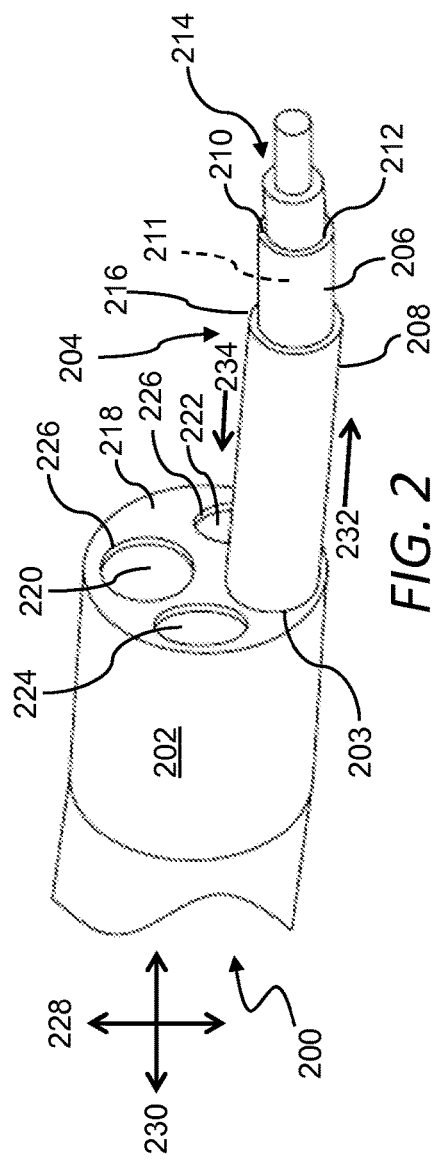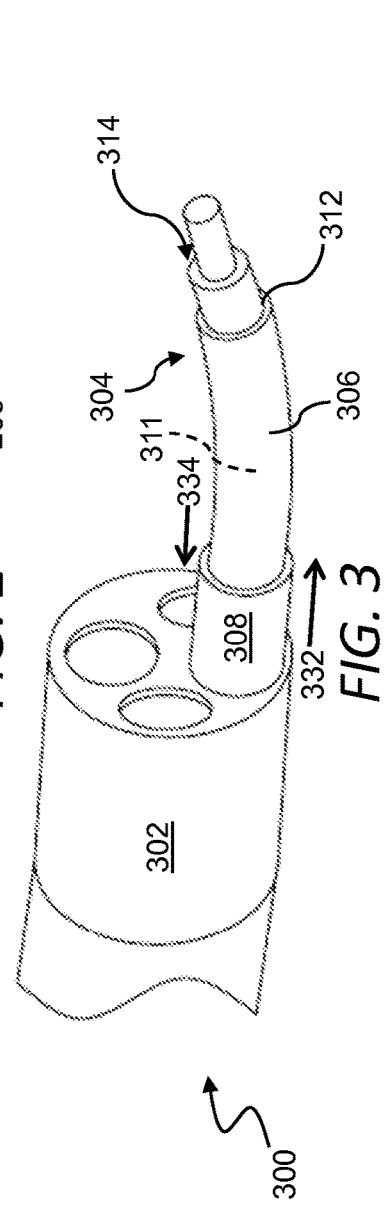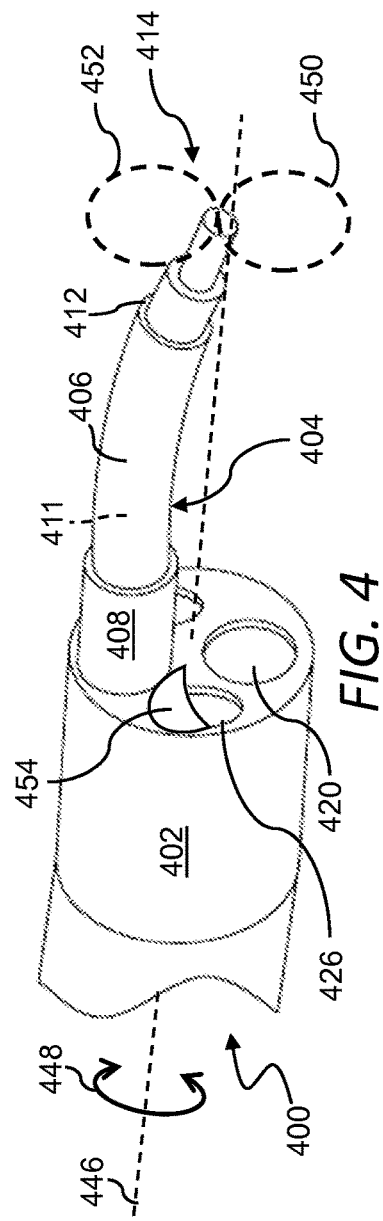

STEERING TECHNIQUES FOR SURGICAL INSTRUMENTS

CROSS-REFERENCE TO RELATED APPLICATIONS

This application claims the benefit under 35 U.S.C. § 119(e) of U.S. Provisional Application No. 61/907,812 filed on Nov. 22, 2013 and U.S. Provisional Application No. 62/057,415 filed on Sep. 30, 2014, where the entire content of each is hereby incorporated by reference.

GOVERNMENT LICENSE RIGHTS

This invention was made with government support under Contract No. FA8721-05-C-0002/MIT-LL-IR10-544 awarded by the United States Air Force. The government has certain rights in the invention.

TECHNICAL FIELD

The present disclosure generally relates to steering techniques for surgical instruments, and more specifically to laser fiber steering using substantially concentric tubes for applications in minimally invasive surgeries and the like.

BACKGROUND

In certain endoscopic procedures, a tool is positioned or aimed for use in a surgical procedure. Existing tools such as endoscopic lasers do not generally facilitate steering of the tool independent of the endoscope, and may pose significant physical and mechanical challenges when executing a surgical procedure that requires small movements within a current field of view. There remains a need for improved systems and methods for steering endoscopic tools such as lasers during surgical procedures.

SUMMARY

A steerable endoscopic tool uses concentric sleeves of varying curvature to steer a tool tip toward or in the direction of a location of surgical interest. By rotating and/or axially displacing such sleeves relative to one another the tool tip may be maneuvered within a current field of view with several degrees of freedom without any physical movement of an endoscope, thus facilitating improved surgical access and control without complex mechanical systems in the endoscope or at the surgical site.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

FIG. 2 shows a steerable endoscopic tool in a relatively straight state.

FIG. 3 shows a steerable endoscopic tool in a relatively curved state.

FIG. 4 shows a steerable endoscopic tool in a relatively curved and rotated state.

DETAILED DESCRIPTION

Figure 1:
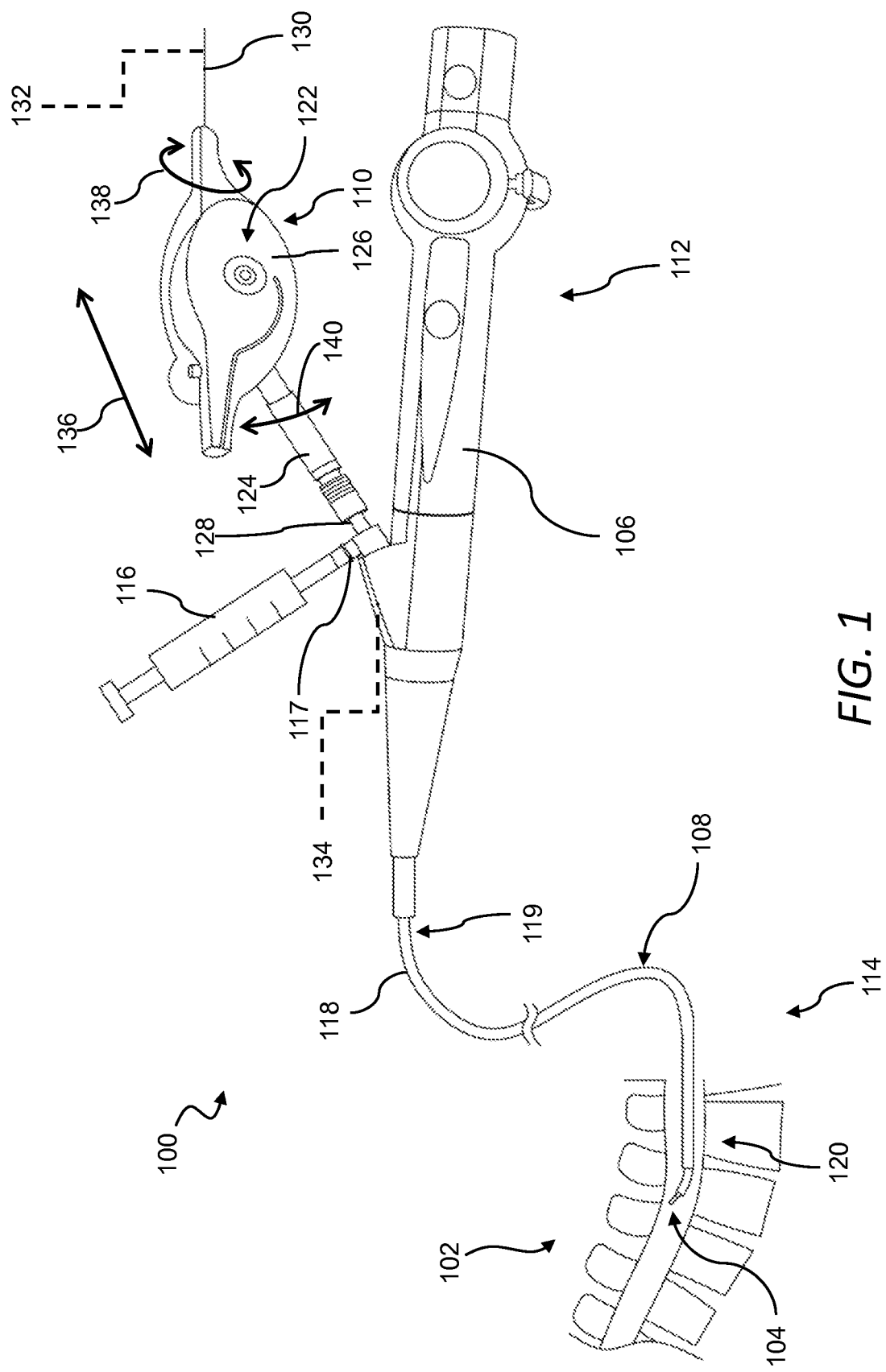
FIG. 1 shows a steerable endoscopic tool traversing a spine.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "backward," "forward," and the like, are words of convenience and are not to be construed as limiting terms.

Described herein are devices, systems, and methods for steering and guiding surgical instruments or surgical tools, and more specifically devices, systems, and methods for laser fiber steering using substantially concentric tubes for applications in minimally invasive surgeries and the like. Although embodiments herein may be described as being directed to surgical instruments for applications in minimally invasive spine surgery (or the like), a person of ordinary skill in the art will recognize that other applications are possible and that applications of the implementations described herein are not limited to those explicitly described in this disclosure. For example, the devices, systems, and methods described herein may be utilized in other surgeries, for instance those that include fiber optics that may advantageously be steered or guided. Other uses outside of the field of surgery are also possible, including without limitation, other fiber optic guidance systems such as those used in the field of plumbing, electrical systems, military or law enforcement applications, and so forth. Stated another way, industries outside of the medical field that have a need for the precision of control of a tool (e.g., controlling laser fiber optics) in space constrained areas that are most easily accessed by scopes or the like may also find the implementations described herein advantageous. Further, although the steering techniques described herein are generally addressing the steering of laser fiber(s) or optical fiber(s), a person of ordinary skill in the art will recognize that other apparatus may also be steered, including without limitation, cameras, cutting tools, ablation tools, material or fluid delivery systems (e.g., medicinal or otherwise), sampling devices, sensors, and so forth.

FIG. 1 shows a steerable endoscopic tool (or simply, "tool 100") traversing a spine. As discussed herein the tool 100 may be configured for use in endoscopic surgery in a surgical site 102 such as a spinal column, or more generally any other space-constrained anatomy by giving a surgeon control of a surgical instrument 104, e.g., a laser fiber optic instrument. Thus, in one aspect, the tool 100 may include an endoscope. More generally, the techniques described herein may be usefully employed in any context where a tool needs to be aimed or positioned within a cavity accessible by an endoscope or similar tool.

As shown in FIG. 1, the main components of the tool 100 may include the surgical instrument 104, a handle 106, a scope 108, and a control mechanism 110. The tool 100 may include a proximal end 112 for controlling the surgical instrument 104 and scope 108, and a distal end 114 for engagement with the surgical site 102.

The surgical site 102 may include a spinal column (e.g. of the spine of a human or other vertebrate) or any other appropriate site. One of ordinary skill in the art will recognize that the spinal column of FIG. 1 is shown by way of example only, and that it may be replaced by another element of anatomy or by an inanimate object, e.g., a pipe or the like. In other words, the surgical site 102 may include inanimate objects, or components or areas of inanimate objects. In one implementation, the tool 100 is designed to provide a surgeon with control over both the surgical instrument 104 and the scope 108 inside of the surgical site 102, e.g., through a spinal column during a minimally invasive spine surgery.

The surgical instrument 104 may include a laser fiber optic instrument. Alternatively, the surgical instrument 104 may also or instead include a camera, a cutting tool (e.g., a mini-scissor), a bipolar probe, a drill, an ablation tool, a material or fluid delivery system, a device for taking/testing a sample, a sensor, and so forth. The surgical instrument 104 may be introduced to a surgical site 102 through a tube, such as the tube forming the working channel of an endoscope. As used throughout this disclosure any reference to surgical instruments shall include surgical tools and vice-versa. Also, as used throughout this disclosure, a fiber optic shall include a laser fiber or laser fiber optic, and vice-versa. The surgical instrument 104 may be disposed within the scope 108 where it extends from a first end 119 of the scope 108 to a second end 120 of the scope 108. In an embodiment where the surgical instrument 104 includes a fiber optic 130, a laser source 132 may be coupled to the fiber optic 130, e.g., at the proximal end 112 of the tool 100. In an implementation including a camera, the tool 100 may include a display 134 or the like that is coupled to the camera through a channel in the flexible endoscopic body. Where the surgical instrument 104 includes a laser fiber optic instrument, the laser may be approved for surgical use, be fiber coupled, be designed to obtain shallow optical penetration depth in tissue, and so forth. For example, a 266 nm, 5 ns laser may be used.

The handle 106 may include a housing 122 designed for engagement by a surgeon in guiding and controlling the scope 108, e.g., an endoscope. The handle 106 and scope 108 may be designed for engagement with the control mechanism 110 and a fluid source 116. In one aspect, the handle 106 includes a commercially available surgical scope device, for example, an Invisio® DUR®-D ureteroscope or similar. In an implementation, movement of the handle 106 yields movement of the scope 108 and/or movement of the surgical instrument 104.

The scope 108 may include an endoscope as commonly known in the art. The scope 108 may include a tube 118, which may form the working channel of an endoscope in an implementation. The scope 108 may also or instead include a flexible endoscopic body (i.e., housing the tube 118, or comprising the tube 118 itself) having a first end 119 and a second end 120. The first end 119 of the scope 108 may be engaged with the handle 106 and the second end 120 may be designed for traversing the surgical site 102. The second end 120 of the scope 108 may include the surgical instrument 104 or a portion thereof. In an aspect, the scope 108 may include nested tubes. One or more of the nested tubes may extend through the entire length of the scope 108, i.e., from the first end 119 to the second end 120, or one or more of the nested tubes may extend through only a portion of the length of the scope 108, or any combination thereof.

The control mechanism 110 may be attached to the handle 106 at the proximal end 112 of the apparatus 100, i.e., toward the first end 119 of the scope 108, where the proximal end 112 of the apparatus 100 may also be referred to herein as the control end. As shown in FIG. 1, the control mechanism 110 may be attached to a top portion of the handle 106 so as to not interfere with the operation and ergonomics of the handle 106, e.g., when a surgeon is guiding the scope 108 using the handle 106. The control mechanism 110 may include a housing 122 and a scope attachment mechanism 124. The housing 122 may include a substantially bulbous portion 126 that is designed to act as an ergonomically friendly component when steering the surgical instrument 104 with the control mechanism 110. The scope attachment mechanism 124 may include a scope attachment interface 128 that forms an engagement with the handle 106. The scope attachment mechanism 124 may generally act as a rotary joint for the control mechanism 110. Although the control mechanism 110 is shown attached to the handle 106 in FIG. 1, other attachment locations may be possible on the tool 100, e.g., including but not limited to below the handle 106, in front of the handle 106, behind the handle 106, and so forth.

The control mechanism 110 may be generally designed to provide control for the surgical instrument 104, which may be independent to control of the scope 108 (e.g., where control of the scope 108 is provided by the handle 106). Thus, in an implementation, steering of a laser fiber optic may be performed through a second level of control independent of that given by an endoscope steering system. The control mechanism 110 may enable control of the surgical instrument 104 in three or more motions, including without limitation, rotation, curvature, and translation. These motions are described below in more detail. The control mechanism 110 may include one or more controls configured to create these motions, e.g., a first control, a second control, a third control, and so forth. In one aspect, the control mechanism 110 controls the motion of one or more nested tubes, which may include a fiber optic 130 as shown in FIG. 1 protruding from the proximal end of the control mechanism 100. The nested tubes may be located inside of the tube 118 that forms the working channel of an endoscope in an implementation. Thus, a method of implementing the tool 100 described herein may include inserting the nested tubes into the scope 108.

Physical manipulation of the control mechanism 110 by a user may enable control of the surgical instrument 104. In an implementation, translation of the surgical instrument 104 is controlled by moving the control mechanism 110 in the directions shown by arrows 136. In an implementation, rotation of the surgical instrument 104 is controlled by rotating the control mechanism 110 in the directions shown by arrows 138. In an implementation, curvature of the surgical instrument 104 is controlled by swiveling the control mechanism 110 in the directions shown by arrows 140.

The fluid source 116 may be a syringe as shown in FIG. 1, e.g., a typical syringe as known in the art for injecting a fluid into the surgical site 102. The fluid source 116 may instead be another source of fluid, including without limitation a housing, container, vial, bottle, drum, and so forth, that contains a fluid. The fluid source 116 may contain a fluid for cooling. For example, the fluid may be used for cooling a surgical site 102, e.g., tissue cooling. The fluid source 116 may also or instead be utilized for pressurization, e.g., pressurizing an area of a surgical site 102 in order to clear a field of view for a sensor (e.g., a lens of a camera). The fluid source 116 may also or instead contain a fluid for cleaning one or more of the surgical instruments 104 disposed at the second end 120 of the scope 108. For example, the fluid may be used for lens cleaning, where one or more of the surgical instruments 104 include visual sensor (e.g., a camera) or light source (e.g., LED). For injecting the fluid into the surgical site, the fluid source 116 may be in communication with the surgical site through a hollow core that leads from the proximal end 112 of the tool 100 to the distal end 114 of the tool 100. The fluid source 116 may include mechanical elements to aid in injecting the fluid into the surgical site, including without limitation, pumps (e.g., hand pump, foot pedal, electrically driven pump, and so forth), valves, pipes, tubes, fittings, couplings, and so forth.

The fluid source 116, handle 106, control mechanism 110, or any combination thereof may be configured for engagement with each other. For example, the fluid source 116 may attach to the handle 106 via a fluid port 117. The fluid port 117 may be disposed in the front of the handle 106 as shown in FIG. 1, or the fluid port may be located elsewhere in the tool 100. For example, the fluid port may be located on the control mechanism 110. Also, the location of the fluid port may depend on whether the fluid is being used for cleaning (e.g., cleaning a lens of the camera) or for cooling. In one aspect, if the fluid is for cleaning, the fluid may run external to the surgical instrument 104, which may include concentric tubes that may be independently steered. In this aspect, the fluid port may be located slightly above the location shown in FIG. 1 on the scope attachment mechanism 124. In another aspect, if the fluid is running internal to the tubing (e.g., for cooling), the fluid port may be located at the back end of the control mechanism 110 near where the fiber optic 130 is shown. The fluid may also be utilized for flushing a surgical site or the like, or for other purposes as will be apparent to one skilled in the art. The tool 100 shown in FIG. 1 may allow for one handed steering and flushing. The fluid may include saline or the like.

The tool 100 of FIG. 1 may be useful for endoscopic surgeries in space-constrained anatomies where fine control of a surgical instrument 104, and more specifically aiming or positioning of the surgical instrument 104, through a working channel of a scope 108 is desired. By way of example, the tool 100 of FIG. 1 may be configured to be used in a spinal decompression procedure. To this end, the surgical instrument 104 may be configured to perform an ablation of ligamentum flavum, where the scope 108 is introduced through the sacral hiatus. The tool 100 may also enable improved treatment of spinal decompression due to discs, bone growth, cartilage, and so forth. The tool 100 may also provide for the ablation of tumors in a surgical site 102, e.g., the spinal canal.

Specifically, the tool 100 may be configured for treating spinal stenosis, and even more specifically for decompressing the spinal canal through removing compressive ligamentum flavum. In use, the tool 100 may first access the spinal epidural space with the scope 108 via the sacral hiatus. A visual sensor may then be utilized to visualize pathologic tissue, and the surgical instrument 104 (i.e., a surgical laser) may be used to remove tissue. The surgical laser may be placed anywhere in the field of view of the visual sensor, and a light source (e.g., LED) may be used to enable proper viewing. The control mechanism 110 may be utilized for guiding the surgical laser to perform the ablation of tissue. Additionally, the tool 100 may be applied to other surgical needs requiring fine tool control and acute visualization within space-constrained anatomies.

In general a positioning system may use nested sleeves, each with a predetermined curvature, to control a bend of the tool tip for aiming and positioning. In one aspect, an outer sleeve is straight and an inner sleeve is curved. By extending the inner sleeve beyond the outer sleeve (or alternatively retracting the outer sleeve to avoid axial displacement of the tool tip) a curvature may be imparted onto the tool, and the tool may be re-straightened by repositioning the outer sleeve around the end of the inner sleeve. This relative axial displacement may be controlled by the control mechanism 110 described herein, or any other suitable electro-mechanical system for controlling relative position. This generally configuration is described in greater detail below. However, it will be appreciated that other configurations are possible. For example, in one embodiment the inner sleeve may be straight and the outer sleeve may be curved. In still another embodiment, both sleeves may be curved, and positioning may be controlled by rotating the two sleeves relative to one another about a shared axis. This latter embodiment is discussed below with reference to FIG. 11.

FIG. 2 shows a steerable endoscopic tool in a relatively straight state. More specifically, FIG. 2 shows the distal end of a tool 200, which may include a scope 202 and one or more nested tubes 204 included within a working channel 203 of the scope 202.

The one or more nested tubes 204 may in general be concentric tubes. The nested tubes 204 may include an inner tube 206 and a sleeve 208. The nested tubes 204 may be controlled by a control mechanism (not shown in FIG. 2) that is located at a remote location from the portion of the nested tubes 204 shown in FIG. 2, i.e., distal to the nested tubes 204.

The inner tube 206 may include a curved tube having an end 210 or terminal portion with a predetermined radius of curvature and a predetermined stiffness. The inner tube 206 may include a hollow core 211 and an exit 212 from the hollow core 211 for a surgical tool 214. The inner tube 206 may be disposed inside of and concentric with the sleeve 208, where it may be free to controllably slide into and out of the sleeve 208 as explained in more detail below. In one aspect, the end 210 of the inner tube 206 may be formed of a shape memory alloy. In another aspect, the end 210 of the inner tube 206 may be formed of nickel titanium ("nitinol") or other material that provides a suitably high stiffness and elasticity to bend and recover shape over multiple movements of the tool 200. The predetermined radius of curvature may be enabled through shape setting the inner tube 206 using any suitable techniques.

In one aspect, the inner tube 206 is disposed within a flexible endoscopic body (i.e., the scope 202). The inner tube 206 may extend through the scope 202, where the inner tube has a first end (not shown) that is distal from its exit 212. The exit 212 of the inner tube 206 may include an orifice from the hollow core 211 designed to house the surgical tool 214.

The sleeve 208 may be slidably disposed outside of and concentric with the inner tube 206. The sleeve 208 may include a terminal portion 216 that is proximal to the end 210 of the inner tube 206. The sleeve 208 may include a stiffness that is greater than the predetermined stiffness of the inner tube 206 and a radius of curvature that is greater than the predetermined radius of curvature of the inner tube 206 (i.e., the sleeve 208 has less curvature than the inner tube 206). In this manner, the sleeve 208 may drive the tool 200 into a straighter (i.e., greater radius of curvature where the tool 200 has less curvature) shape by extending over the more curved inner tube 206. As shown in FIG. 2, the terminal portion 216 of the sleeve may be substantially straight. In an aspect, the terminal portion 216 of the sleeve may be formed of nitinol.

In an aspect, the inner tube 206 may be positioned to extend slightly beyond the sleeve 208 (e.g., in a default position of the control mechanism described above), and the inner tube 206 may have a distal tip (i.e., end 210) that is slightly curved. In one aspect, the curvature of the inner tube 206 (i.e., distal tip of the inner tube 206) may be such that when the inner tube 206 is extended beyond the sleeve 208, which has a dominating stiffness, the inner tube 206 is able to curve. In one aspect, the relative stiffness and curvature of these two concentric tubes may be selected so that when fully extended from the sleeve 208, the inner tube 206 reaches, or has an aim that reaches, a perimeter of a visual sensor of the tool 200. As described herein, in one aspect, by sliding the sleeve 208 relative to the inner tube 206, the curve at the distal tip of the inner tube 206 may be changed.

The surgical tool 214 may include a laser fiber disposed in the hollow core 211 of the inner tube 206. The surgical tool 214 may also or instead include other tools as described herein or otherwise known in the art.

As shown in FIG. 2, the scope 202 may form a casing about the inner tube 206 and the sleeve 208. The scope 202 or casing may form an endoscopic tool. The scope 202 may include a remote end 218 that houses one or more other surgical tools distinct from the surgical tool 214 engaged with the nested tubes 204. For example, as shown in FIG. 2, these other surgical tools may include a second surgical tool 220, a third surgical tool 222, and a fourth surgical tool 224. One skilled in the art will recognize that more or less other surgical tools may be included in implementations without departing from the scope of this disclosure. The second surgical tool 220, third surgical tool 222, and fourth surgical tool 224 may be disposed proximal to the end 210 of the inner tube 206 relative to the entire tool 200. The second surgical tool 220, third surgical tool 222, and fourth surgical tool 224 may be disposed in channels 226 for coupling them to a control end (not shown in FIG. 2) of the tool 200. The other surgical tools may include, without limitation, one or more of a laser fiber, a camera, a sensor, an illumination source, a cutting tool (e.g., a mini-scissor), a bipolar probe, a drill, an ablation tool, a material or fluid delivery system, a device for taking/testing a sample, and so forth. For example, in one aspect, the second surgical tool 220 includes a visual sensor (e.g., a camera), and both the third surgical tool 222 and the fourth surgical tool 224 include illumination sources (e.g., LEDs). In another aspect, at least one of the channels 226 forms a hollow core for fluid to be supplied from a fluid source (e.g., syringe or the like), through the scope 202 and out of the remote end 218 of the scope 202.

The tool 200 may be controlled by a control system that includes a control mechanism (not shown in FIG. 2) for controlling the motion of the nested tubes 204 relative to one another, such as by facilitating an axial displacement of the inner tube 206 relative to the sleeve 208 (or vice versa). For example, the control mechanism may include a control configured to change a curvature of the end 210 of the inner tube 206 by axially displacing the sleeve 208 relative to the inner tube 206. The control mechanism may also or instead include a control configured to axially translate the end 210 by substantially uniformly axially displacing the inner tube 206 and the sleeve 208 together, such as to deploy the tip of the tool 200 from an endoscopic enclosure. The control mechanism may also or instead include a control configured to axially rotate the inner tube 206 within the sleeve 208. The control mechanism may also or instead include a control configured to axially rotate both the sleeve 208 and the inner tube 206 together within the scope 202. The control for enabling one of the movements described herein may be a separate control than the controls for enabling another one of the movements described herein. Alternatively, the same control may enable all of the movements described herein. In other words, the control mechanism may include one or more controls (e.g., a first control, a second control, a third control, and so forth), where each of the one or more controls separately enables the motions described above, or the control mechanism may include only one control that enables all movements.

The one or more nested tubes 204 may be formed of different materials from one another or they may be formed of the same material. Similarly, each one of the one or more nested tubes may be formed of one material, or they may be formed of two or more materials. Some examples of materials that may be used for the one or more nested tubes 204 include metals, polymers, elastomers, composites, shape memory alloys (e.g., nitinol), and so forth, as well as any combinations thereof. In general, any materials or composites with sufficient rigidity and elasticity to operate as described herein may be usefully employed as the material of the tube and sleeve as contemplated herein.

Although the implementations may come in different shapes and sizes as will be apparent to a person of ordinary skill in the art, the following dimensions are provided by way of example to understand one such implementation. In one aspect, the sleeve 208 has an outer diameter of approximately 1.12 millimeters, the inner tube 206 has an outer diameter of approximately 0.86 millimeters, the surgical tool 214 has an outer diameter of approximately 0.41 millimeters, and the radius of curvature of the end 210 of the inner tube 206 relative to the sleeve 208 is approximately 3.56 millimeters. In another aspect, the hollow core 211 has a diameter of at least one millimeter. However, it shall be understood that these dimensions are provided by way of example only and can vary greatly depending on use or any other number of factors. Further, although the shape of the tool 200 is generally shown herein as a tube-shape (i.e., cylindrical shape), other shapes are possible including shapes with polygonal cross-sections such as squares, triangles, hexagons, and so forth.

Using a guiding mechanism such as the handle of an endoscopic tool, the entire tool 200 of FIG. 2 may be movable, e.g., in the directions shown by arrows 228 and 230 (i.e., up and down, forward and backward). Other movements of the tool 200 may also or instead be made possible using a guiding mechanism such as the handle of an endoscopic tool, including without limitation, rotating the entire tool 200. However, these movements can be cumbersome, and it therefore may be desirous to enable movement of the nested tubes 204 independently from the scope 202. To this end, implementations may include a control mechanism (e.g., a control mechanism separate from the guiding mechanism such as the handle of an endoscopic tool, or separately incorporated into the handle of an endoscopic tool). This control mechanism is described in detail elsewhere herein, but exemplary movements made possible by such a control mechanism will now be described with reference to FIGS. 2-4.

As stated above, FIG. 2 depicts a tool 200 deployed as a relatively straight tool or substantially straight, i.e., with a relatively large radius of curvature. The relatively straight configuration may be enabled through the configuration of the inner tube 206 and the sleeve 208. For example, in one aspect, the sleeve 208 is substantially straight when no outside forces are acting upon it, and the inner tube 206 is substantially curved when no outside forces are acting upon it (i.e., the sleeve 208 has a greater radius of curvature than the inner tube 206). In this configuration, the sleeve 208 may have a greater stiffness than the stiffness of the inner tube 206, with a resulting overall straightness of the combined sleeve 208 and inner tube 206. In an aspect, when the sleeve 208 is axially displaced in the direction of arrow 232 and it covers more of the inner tube 206, as shown in FIG. 2, the nested tubes 204 of the tool 200 will provide a straighter shape. The control mechanism described throughout this disclosure enables this axial movement of at least one of the sleeve 208 and the inner tube 206 to axially displace the sleeve 208 relative to the inner tube 206 in the directions shown by arrows 232 and 234 in order to impart or remove a curvature from the tool 200.

FIG. 3 shows a steerable endoscopic tool in a relatively curved state. Similar to FIG. 2, the tool 300 of FIG. 3 shows a scope 302 and nested tubes 304 such as any of the nested tubes described above, where the nested tubes 304 include an inner tube 306 and a sleeve 308, and where the inner tube 306 includes a hollow core 311 with an exit 312 that houses a surgical tool 314. The configuration of the tool 300 in FIG. 3 may be made possible through a control mechanism causing the sleeve 308 to move in the direction shown by arrow 334. Specifically, in the embodiment shown in FIG. 3, because the sleeve 308 has a greater radius of curvature than the inner tube 306 (i.e., the sleeve 308 is relatively straighter than the inner tube 306), and because the sleeve 308 has a greater stiffness than the stiffness of the inner tube 306, when the sleeve 308 is axially displaced relative to the inner tube 306 in the direction shown by arrow 334 such that the sleeve 308 covers less of the inner tube 306, the nested tubes 304 of the tool 300 will tend to curve. In an aspect, if the sleeve 308 is axially displaced relative to the inner tube 306 in the direction shown by arrow 332 such that the sleeve 308 covers more of the inner tube 306, the configuration would more closely resemble that of FIG. 2, where the tool 300 will tend to straighten.

Therefore, as described above, the radius of curvature of the nested tubes 304 may be controlled by axial displacement of the inner tube 306 relative to the sleeve 308 and may vary in proportion to the amount that the inner tube 306 extends from the sleeve 308. Where the sleeve 308 is axially displaced to cover more of the inner tube 306, the tool 300 will have a greater radius of curvature (i.e., it will be straighter) than nested tubes 304 where the sleeve 308 is axially displaced to cover less of the inner tube 306. Thus, an implementation enables a user to vary the instantaneous curvature of the inner tube 306 by sliding the sleeve 308 relative to the inner tube 306. In one aspect, the movement of the sleeve 308 relative to the inner tube 306 is geared within the control mechanism at a ratio such that a user can achieve fine control of the curvature with movements of magnitude reasonable for human hand control. However, one of ordinary skill will recognize that the gearing ratio may vary in different implementations. Also, it will be understood that all movements described herein may be geared at a ratio such that a user can achieve fine control of movement of the tool/scope apparatus or components thereof with movements of magnitude reasonable for human hand control.

FIG. 4 shows a steerable endoscopic tool in a relatively curved and rotated state. The tool 400 may be any of the tools described above. Similar to FIGS. 2 and 3, the tool 400 of FIG. 4 shows a scope 402 and nested tubes 404, where the nested tubes 404 include an inner tube 406 and a sleeve 408, and where the inner tube 406 includes a hollow core 411 with an exit 412 that houses a surgical tool 414. The configuration of the tool 400 may be achieved by rotating one or more of the scope 402, the inner tube 406, and the sleeve 408, thus facilitating steerage of the tool 400 within a field of view and/or across a surgical site. This movement may be controlled with a control mechanism such as any of the control mechanisms described above where, for example, a rotation of the entire control mechanism may cause a corresponding rotation of the tool 400, such as a rotation around a central axis 446 of the tool 400 in the direction of arrows 448. Specifically, the tool 400 in FIG. 4 is shown axially rotated 180 degrees from the tool shown in both FIGS. 2 and 3.

In addition to the rotation shown in FIG. 4, which is a rotation of an entire scope 402 about an axis, axial rotation of the nested tubes 404 independent from the scope 402 may also be possible, e.g., using the same control mechanism or a different control mechanism. Further, axial rotation of the inner tube 406, sleeve 408, surgical tool 414, or other components (e.g., second surgical tool 420) independent from the scope 402 may also be possible, e.g., using the same control mechanism or a different control mechanism. For example, in one aspect, the control mechanism includes a control for axially rotating the inner tube 406 within the sleeve 408. As noted above, this operation may be particularly useful where both the inner tube 406 and the sleeve 408 are curved, so that various degrees of straightness or curvature can be imparted by rotating one curved element within another. In another aspect, the control mechanism includes a control for axially rotating the nested tubes 404 together. In yet another aspect, the control mechanism includes a control for axially rotating the sleeve 408 relative to one or more of the scope 402 and the inner tube 406.

The control mechanism may thus enable axial rotation of the entire tool 400, the nested tubes 404, a single one of the nested tubes 404, or any combination thereof. In general, three hundred sixty degree rotation is contemplated, although greater rotation may also be possible, e.g., where the tool 400 is rotated multiple times in the same direction. Lesser rotation may also be useful in a variety of circumstances, particularly where the entire endoscope can be independently rotated to provide a certain degree of rotational freedom independently from the tool 400. Bearings or the like may be provided to facilitate rotation of the tool 400 or components thereof.

The axial rotation of the scope 402 may allow for the tracing of a first arc 450 at the distal end of the nested tubes 404, e.g., at the end of the surgical tool 414. The radius of the first arc 450 may be defined by the curvature of the inner tube 406, and thus the first arc 450 may be smaller when the nested tubes are rotated and configured as in FIG. 2, and the first arc 450 may be larger when the nested tubes are rotated and configured as in FIG. 3. This may be useful in providing for a sweeping motion of the surgical tool 414 over a controllable arc.

The axial rotation of the nested tubes 404 may allow for the tracing of a second arc 452 at the distal end of the nested tubes 404, e.g., at the end of the surgical tool 414. Similar to the above, the radius of the second arc 452 may be defined by the curvature of the inner tube 406, and thus the second arc 452 may be smaller when the nested tubes are rotated and configured as in FIG. 2, and the second arc 452 may be larger when the nested tubes are rotated and configured as in FIG. 3. This may be similarly useful in providing for a sweeping motion of the surgical tool 414 over a controllable arc.

Other movements separate from those described above with reference to FIGS. 2-4 may also be possible. For instance, as explained above, translation of the entire scope apparatus may be made possible by a guiding mechanism such as the handle of an endoscopic tool. Additionally, translation (i.e., advancement and retraction) of the nested tubes (individually or together) may be made possible by the guiding mechanism or by the control mechanism as described herein. For example, relative to the end or terminal portion of the scope, the control mechanism may enable the nested tubes to fully retract into the scope or to deploy from the scope at varying lengths. This may facilitate storage and deployment of the tool between large scale operations such as insertion into or retraction from a surgical site. The translational movement for tool deployment (concurrent axial displacement of both nested tubes 404) may be geared at a ratio such that a user can achieve fine control of the translation with movements of magnitude reasonable for human hand control. However, one of ordinary skill will recognize that the gearing ratio may vary in different implementations.

The movements shown and described with reference to FIGS. 2-4 above may be useful in an embodiment where the tool is an endoscope and the surgical tool is a laser fiber optic for laser ablation of tissue during surgery. For example, the movements allowed through the control mechanism may enable the precise laser ablation of tissue by providing a laser fiber optic with a second level of mechanical control beyond that given by simply the steering of the endoscope. This may allow a surgeon to, from a fixed endoscope head position, precisely position or continuously sweep the distal tip of the surgical tool anywhere within the field of view of the endoscope or otherwise, thereby enabling the precise surgical operation of specific and discrete targets. This movement may be particularly useful for the ablation of tissue because the ablation tool may continually sweep over a defined area where the amount of mechanical clearance between the ablation tool and the endoscope working channel may preclude tight control in the lateral directions. For example, in space constrained areas such as the spinal column, there is often little room to move an endoscope laterally.

The movements shown and described with reference to FIGS. 2-4 above may also or instead be useful for cleaning or cooling a surgical site using a fluid source. Specifically, the movements described herein may provide for control over the direction of flow of a fluid. For example, in an implementation, a fluid source may be in communication with one or more of the nested tubes, e.g., the fluid may travel through one of the nested tubes, in between the nested tubes, or around one or more of the nested tubes. In one aspect, the fluid travels from a fluid source to a surgical site through the inner tube such that it exits the inner tube at its end around the surgical tool (e.g., a laser fiber). In this manner, the steering of the nested tubes may permit control over the direction of flow of the fluid in a surgical site. This may be useful for directing the flow of fluid toward a specific surgical area, toward the face of a lens of a camera, and so forth.

The fluid may also or instead exit through a channel included in the distal end of the scope, for example, the fluid may exit through the channel 426 shown in FIG. 4. The channel 426 may be in communication with a scoop 454 or the like that is designed to redirect the fluid. In the implementation shown in FIG. 4, the scoop 454 is shaped and positioned about the channel 426 to direct fluid exiting the channel 426 toward the second surgical tool 420, which may be the lens of a camera. This may be useful in cleaning the lens of the camera. The steering provided by the techniques described herein may further permit control over the direction of flow of the fluid in this aspect. For example, the nested tubes 404 may be steered in a manner that can further redirect the fluid exiting from the channel 426 of the scope 402, or the scope 402 may otherwise be steered to direct the flow of fluid exiting from the channel 426.

Figure 5:
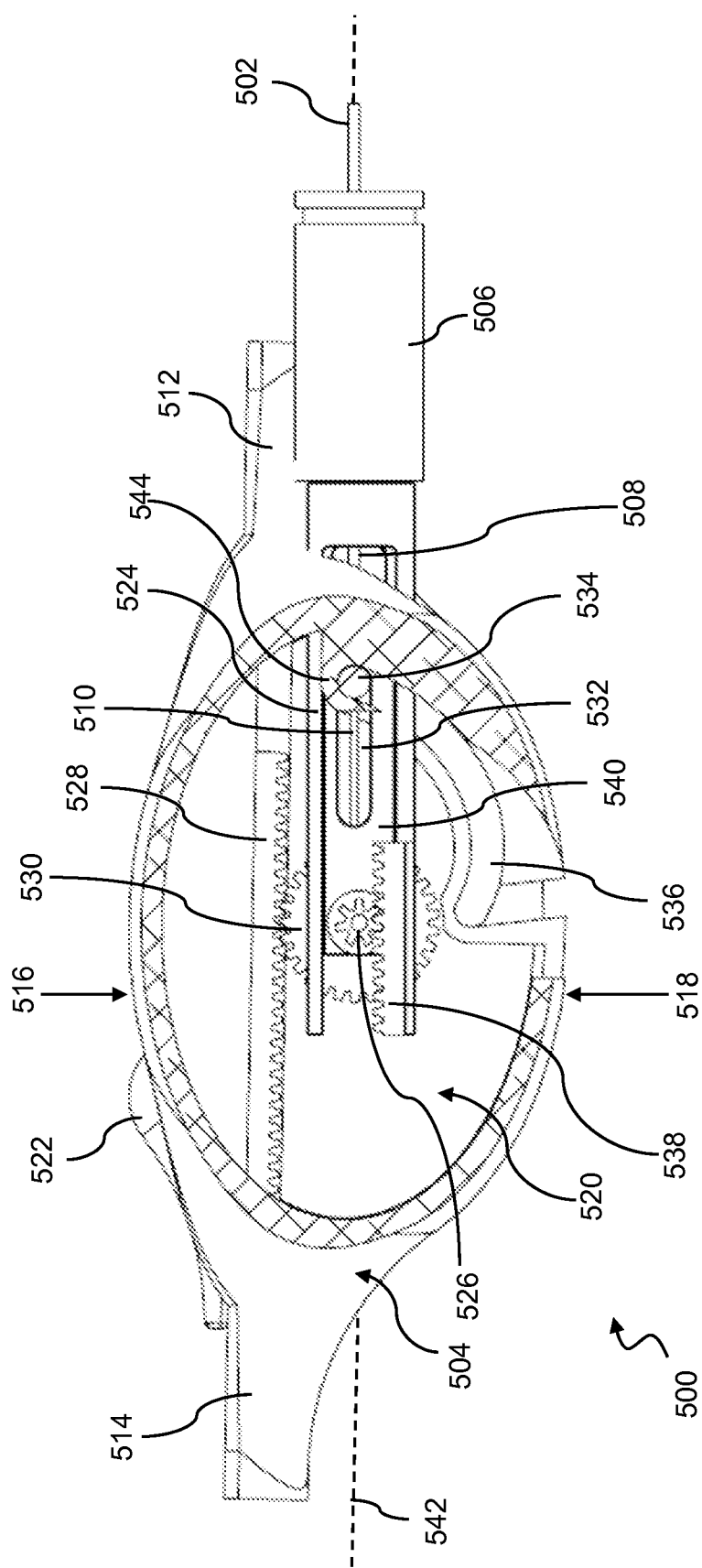
FIG. 5 is a cross-section of a control mechanism for a steerable endoscopic tool.

FIG. 5 is a cross-section of a control mechanism for a steerable endoscopic tool. As discussed above, a scope apparatus may include a guiding mechanism such as the handle of an endoscopic tool, which may include, may be supplemented by, or may be replaced by a control mechanism, such as the control mechanism 500 shown in FIG. 5. The control mechanism 500 may be configured to mechanically control motion of nested tubes such as those described above relative to an endoscope or similar tool. The control mechanism 500 may be positioned on the proximal end of an endoscope or the like as generally described herein, and may be engaged with the nested tubes 502 through the working channel of the scope such that by moving the control mechanism 500 or a component thereof, movement of the nested tubes 502—rotation, relative axial displacement, etc.—may be achieved. In one aspect, movements of the control mechanism 500 relative to another portion of the scope apparatus such as the body of an endoscope may translate into steerage of the tool at the distal end of the endoscopic tool.

As discussed above, the control mechanism 500 may be engaged to the nested tubes 502 through mechanical control wires or the like for controlling movement of the nested tubes, including without limitation controlling translational movement, controlling curvature, and controlling rotational movement. It will be appreciated that the control mechanism 500 may, in various embodiments, be coupled to the nested tubes 502 through mechanical control wires, or coupled to the nested tubes through a pair of concentric sleeves (preferably with low-friction, complementary surfaces), or coupled directly to the ends of the nested tubes 502. Although emphasis in the following description is upon direct coupling to an inner and outer tube of the nested tubes 502, all such configurations suitable for mechanically coupling the control mechanism 500 to the nested tubes 502 to facilitate relative axial displacement are intended to fall within the scope of this disclosure. The control mechanism 500 may generally include a housing 504 that holds mechanical components for controlling movement of the nested tubes 502 and a scope attachment mechanism 506 engaged with the housing 504 for connecting the housing 504 to a scope apparatus, e.g., the working channel of an endoscope. In one aspect, the control mechanism 500 is constructed from two main parts—the housing 504 and the scope attachment mechanism 506, where these components are slidably and rotatably engaged. In an implementation, the scope attachment mechanism 506 fixedly engages with a scope apparatus, while the housing 504 is movably engaged to the scope attachment mechanism 506. For example, the housing 504 may be able to translate, rotate, or swivel relative to the scope attachment mechanism 506. As discussed herein, the nested tubes 502 may include an outer tube 508 (otherwise referred to herein as a sleeve) and an inner tube 510. As noted above, while the description emphasizes direct coupling to the outer tube 508 and inner tube 510, similar control over axial displacement may be achieved with a variety of forms of mechanical coupling to the nested tubes 502.

In general, the housing 504 may facilitate axial displacement of one nested tube relative to another as described herein. The housing 504 may be shaped for a user to grip and manipulate the control mechanism 500 relative to the scope attachment mechanism 506. To this end, the housing may include a front handle 512, a rear handle 514, a top portion 516, a bottom portion 518, and a central portion 520. The front handle 512 may be disposed adjacent to the scope attachment mechanism 506, where a top surface of the front handle 512 includes a slot for the sliding of a finger interface 522 that is part of a tubing advancement mechanism. The rear handle 514 may protrude from the rear of the central portion 520 of the housing 504 and may also include a portion of a slot for the sliding of the finger interface 522. In FIG. 5, the finger interface 522 is disposed adjacent to the rear handle 514, but it may move back and forth along the top portion 516 of the housing 504 in the slot. The rear handle 514 may also include an orifice where the scope, the nested tubes 502, the surgical tool (e.g., laser fiber), or any combination thereof, may protrude through the control mechanism 500 and out of the orifice of the rear handle 514. In this manner, devices may be engaged with the scope, the nested tubes, the surgical tool, and so forth, including without limitation a laser source, a display for a camera, a fluid source, and so forth. The central portion 520 may include a substantially bulbous shape, and may be substantially hollow to allow the central portion 520 to house mechanical elements for controlling relative axial movement of the nested tubes 502.

The mechanical elements included within the housing 504 may include support rails 524, an axle 526, a tubing advancement slide rack 528, a tubing advancement gear 530, a slider channel 532, an outer tube attachment rod 534, a curvature adjustment channel 536, a support rail slide rack 538, and a tube attachment slider 540. In one aspect, the support rails 524, slider channel 532, and the support rail slide rack 538 may be included on the scope attachment mechanism 506 or engaged to the scope attachment mechanism 506, while the other aforementioned mechanical elements are included on or within the housing 504. The housing 504 and the scope attachment mechanism 506 may be coupled via the axle 526, other components, or any combination thereof. The coupling of the housing 504 and the scope attachment mechanism 506 may allow for translation, rotation, and swiveling of the housing 504 relative to the scope attachment mechanism 506.

The mechanical elements that make up a tubing advancement mechanism, which may be used for controlling advancement and refraction of the nested tubes 502 (i.e., translational movement of either or both of the nested tubes 502) will now be discussed. In general, translational movement of the nested tubes may be caused by translating the housing 504 or components thereof relative to the scope attachment mechanism 506. In one aspect, moving the finger interface 522 from the rear handle 514 toward the front handle 512 will advance the nested tubes, while moving the finger interface 522 from the front handle 512 toward the rear handle 514 will retract the nested tubes. Thus, in this aspect, there exists some form of mechanical engagement between the finger interface 522 and the nested tubes either directly or through a series of mechanical components. More generally, in one aspect, the housing may facilitate axial displacement of both nested tubes 502 together, such as for deployment or retraction of the steerable tip.

In an aspect, the finger interface 522 includes a surface for engagement with a user's finger (or other means for interaction with a user) on the top portion 516 of the control mechanism 500. The finger interface 522 may be engaged with the tubing advancement slide rack 528, which is disposed within the housing 504 of the control mechanism 500, where translational movement of the finger interface 522 causes translational movement of the tubing advancement slide rack 528. The finger interface 522 is slidably engaged with the housing 504 via a slot on the top portion 516 of the housing 504. The tubing advancement slide rack 528 may include a plurality of teeth on a bottom surface thereof that can interface with corresponding teeth on a gear, e.g., the tubing advancement gear 530. In an implementation, translation of the finger interface 522 also causes translation of the housing 504 relative to the scope attachment mechanism 506. In this implementation, the housing 504 may move relative to the support rails 524 and the support rail slide rack 538, which remain stationary with the scope attachment mechanism 506.

The housing 504 may also include the tubing advancement gear 530 and the axle 526. The tubing advancement gear 530 and the axle 526 may be rotatably coupled within the housing 504, where each may be able to rotate together (i.e., rotating the tubing advancement gear 530 thereby rotates the axle 526) or they may be able to rotate independent of one another. As stated above, the tubing advancement slide rack 528 may cooperate with the tubing advancement gear 530 such that translational movement of the tubing advancement slide rack 528 (e.g., caused by translational movement of the finger interface 522) causes rotation of the tubing advancement gear 530. Thus, in an aspect where rotation of the tubing advancement gear 530 also rotates the axle 526, movement of the tubing advancement slide rack 528 thereby rotates the axle 526. The axle 526 may include teeth or other engagement means for cooperation with another component such as the support rail slide rack 538.

The scope attachment mechanism 506 may be engaged with the support rails 524 that include or are engaged with the support rail slide rack 538. In this manner, because the housing 504 may be engaged to the support rails 524 via the engagement between the axle 526 and the support rail slide rack 538, movement of the housing 504 relative to the support rail slide rack 538 also moves the housing 504 relative to the scope attachment mechanism 506. The support rails 524 may also slidably engage with the tube attachment slider 540, which may engage with the axle 526. In other words, the support rails 524 and the tube attachment slider 540 may be separate components that are slidably engaged relative to one another. The tube attachment slider 540 may include the slider channel 532, which enables movement of the outer tube 510 relative to the inner tube 508 as discussed in more detail below. Movement of the housing 504 relative to the support rails 524 may allow for translational movement relative to the scope attachment mechanism 506, and may be enabled through the axle 526, the support rail slide rack 538, and the tube attachment slider 540. The support rail slide rack 538 may thus include teeth on a top surface thereof that can interface with corresponding teeth on a gear, e.g., the axle 526.

In use, as explained below with reference to FIGS. 6 and 7, advancement and retraction of the nested tubes 502 may be caused by sliding the finger interface 522 along the slot on the top portion 516 of the housing 504. This may cause translational movement of the tubing advancement slide rack 528, which in turn rotates the tubing advancement gear 530 and the axle 526. Rotation of at least one of the tubing advancement gear 530 and the axle 526 may cause translational movement of the housing 504 relative to the support rails 524, which is enabled by the axle 526 rotating along the support rail slide rack 538. Thus, the housing 504 moves forward relative to the scope attachment mechanism 506, or stated alternatively, the support rail slide rack 538 moves backward relative to the housing 504. In an aspect, the movement of the entire housing 504 relative to the scope attachment mechanism 506 translates the nested tubes, which are engaged to the housing 504. In another embodiment, translational movement of the scope attachment mechanism 506 causes translational movement of the nested tubes, i.e., advancement and refraction of the nested tubes. In another yet embodiment, advancement and retraction of the nested tubes may be caused by directly sliding the entire housing 504 relative to the scope attachment mechanism 506 without sliding the finger interface 522.

While a particular mechanical configuration is depicted, it will be understood that any suitable arrangement for controllably advancing the tool without changing curvature may also or instead be employed. It will be noted that the embodiment depicted in FIG. 5 provides a significant change in mechanical advantage so that moving the finger interface 522 most of the length of the housing 504 only moves the tip of the tool a small amount, which provides appropriate visual and tactile feedback for the relatively small motion required to advance and retract the tool tip from the endoscope body. Other gearing ratios may also or instead be used according to user preferences, specifications and so forth.

The mechanical elements that may be used for controlling curvature of the nested tubes 502 will now be discussed. As discussed above, the curvature of the nested tubes may be adjusted through translational movement of the outer tube 508 relative to the inner tube 510. In one aspect, adjusting the curvature includes swiveling the housing 504 relative to the scope attachment mechanism 506 about an axis of a connection point between the housing 504 and the scope attachment mechanism 506 (e.g., the axis of the axle 526). This swiveling motion may release the outer tube attachment rod 534 from a locking protrusion 544. Additionally, once the housing 504 is swiveled and the outer tube attachment rod 534 is released from the locking protrusion 544, adjusting the curvature may then include translating the housing 504 along the axis 542 relative to the scope attachment mechanism 506. Adjusting the curvature of the nested tubes 502 is discussed in more detail with reference to FIG. 8.

The outer tube attachment rod 534 may be engaged with the housing 504 and movable with the housing 504 when it is in an unlocked position. However, in the position shown in FIG. 5, the outer tube adjustment rod 534 may be held in place by a locking protrusion 544, and thus it is in a locked position. The outer tube attachment rod 534 may engage the outer tube 508 but not the inner tube 510 of the nested tubes 502. Thus, moving the outer tube attachment rod 534 (or rather moving the housing 504 and thus the outer tube attachment rod 534 relative to the scope attachment mechanism 506) may move the outer tube 508 but not the inner tube 510. However, because the outer tube adjustment rod 534 may be held in place by a locking protrusion 544, the housing 504 may need to be swiveled relative to the scope attachment mechanism 506 in order to release the outer tube adjustment rod 534 such that it can slide within the slider channel 532 and thus move the outer tube 508 to which it is attached. Thus, in an implementation, swiveling the housing 504 relative to the scope attachment mechanism 506 and then translating the housing 504 relative to the scope attachment mechanism 506 may move the outer tube 508 but not the inner tube 510. The housing 504 may thus be movable relative to the tube attachment slider 540 and vice versa. Thus, in an aspect, when the housing 504 is swiveled relative to the scope attachment mechanism 506 about the axis of the axle 526, the outer tube attachment rod 534 correspondingly moves along the central portion 520 of the housing 504 within the curvature adjustment channel 536 which releases the outer tube attachment rod 534 from the locking protrusion. Because the outer tube attachment rod 534 may be attached to the outer tube 508, translating the housing 504 and thus the tube attachment rod 534 along the axis 542 may cause either the advancement or retraction of the outer tube 508 relative to the inner tube 510, thus adjusting the curvature of the nested tubes 502.

The outer tube attachment rod 534 may be movably situated in the housing 504. Additionally, in an alternate embodiment, when the housing 504 is swiveled relative to the scope attachment mechanism 506 about the axis of the axle 526, the curvature of the nested tubes 502 may be adjusted without the need for translation of the housing 504.

As discussed herein, the scope or nested tubes 502 may also be rotated by the control mechanism 500. The rotation of the scope or nested tubes 502 may occur by rotating the housing 504 of the control mechanism 500. The housing 504 may be rotated relative to the scope attachment mechanism 506, which remains stationary in an embodiment. Alternatively, the scope attachment mechanism 506 may also or instead rotate. Rotation of the housing 504 of the scope attachment mechanism 506 may occur around a rotation axis 542.

Some exemplary movements of the nested tubes caused by the mechanical components of the control mechanism are demonstrated in FIGS. 6-8 and discussed below.

Figure 6:
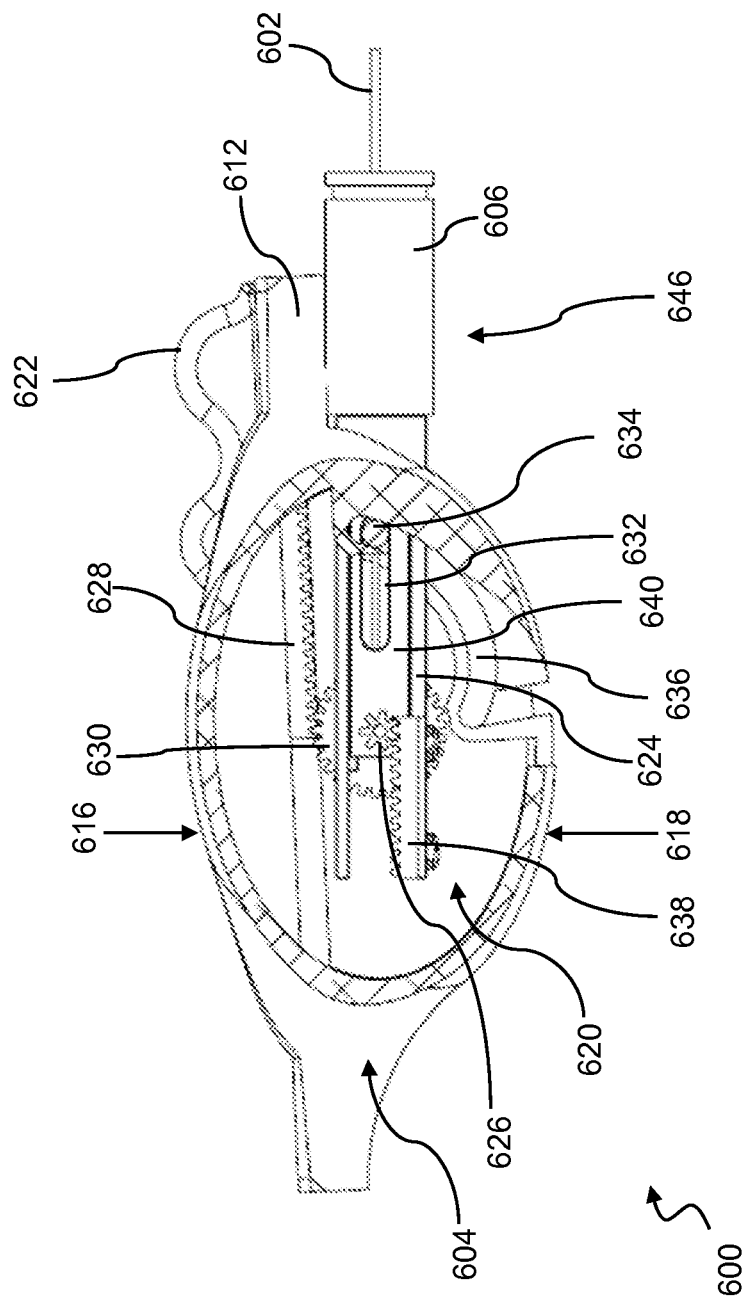
FIG. 6 is a cross-section of a control mechanism in a deployed, straight state.

FIG. 6 is a cross-section of a control mechanism in a deployed, straight state. In other words, in FIG. 6, the control mechanism 600 is positioned such that the nested tubes 602 are each translated forward relative to a scope, which may be a movement independent of translational movement of the scope. FIG. 6 shows a control mechanism 600, nested tubes 602, a housing 604, a scope attachment mechanism 606, a top portion 616, a bottom portion 618, a central portion 620, a finger interface 622, support rails 624, an axle 626, a tubing advancement slide rack 628, a tubing advancement gear 630, a slider channel 632, an outer tube attachment rod 634, a curvature adjustment channel 636, a support rail slide rack 638, and a tube attachment slider 640.

FIG. 6 may include a fully deployed state for the control mechanism 600, where the housing 604 and the finger interface 622 are displaced toward the scope attachment mechanism 606 a maximum length. This may be caused by sliding the finger interface 622 along the slot on the top portion 616 of the housing 604 toward the front end 646 of the housing 604 as far as it may travel, i.e., until it reaches the end of the slot on the top portion 616 of the housing 604 on the front handle 612. When the finger interface 622 is slid forward toward the front end 646 of the housing 604, the tubing advancement slide rack 628 may move forward, which rotates the tubing advancement gear 630, which moves the axle 626 (and thus the housing 604) forward relative to the support rail slide rack 638. Thus, in an implementation, the housing 604 moves forward and thus advances the nested tubes 602.

Figure 7:
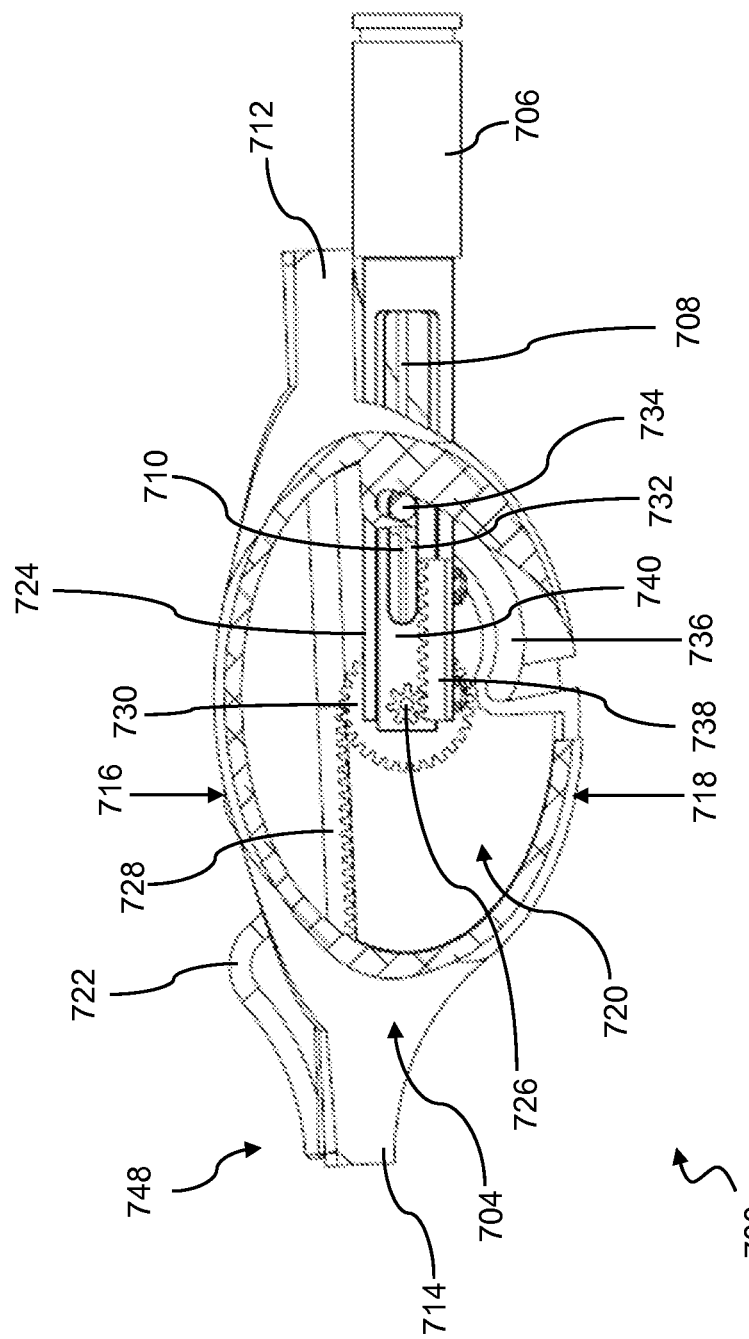
FIG. 7 is a cross-section of a control mechanism in a retracted, straight state.

FIG. 7 is a cross-section of a control mechanism in a retracted, straight state. In other words, in FIG. 7, the control mechanism 700 is positioned such that the nested tubes are translated backward relative to a scope, which may be a movement independent of translational movement of the scope. In other words, in FIG. 7, the nested tubes would be moved toward the scope and possibly into a fully retracted position where they are disposed entirely within the scope on the distal end of the scope. FIG. 7 shows a control mechanism 700, nested tubes, a housing 704, a scope attachment mechanism 706, a top portion 716, a bottom portion 718, a central portion 720, a finger interface 722, support rails 724, an axle 726, a tubing advancement slide rack 728, a tubing advancement gear 730, a slider channel 732, an outer tube attachment rod 734, a curvature adjustment channel 736, a support rail slide rack 738, and a tube attachment slider 740.

As stated above, FIG. 7 may include a fully retracted state for the control mechanism 700 (and the nested tubes), where the housing 704 and the finger interface 722 are displaced away from the scope attachment mechanism 706 a maximum length. This may be caused by sliding the finger interface 722 along the slot on the top portion 716 of the housing 704 toward the back end 748 of the housing 704 as far as it may travel, i.e., until it reaches the end of the slot on the top portion 716 of the housing 704 on the rear handle 714. When the finger interface 722 is slid toward the back end 748 of the housing 704, the tubing advancement slide rack 728 moves backward, which rotates the tubing advancement gear 730, which moves the axle 726 (and thus the housing 704) backward relative to the support rail slide rack 738. Thus, in an implementation, the housing 704 moves backward and thus retracts the nested tubes.

FIG. 7 also depicts a state in which the nested tubes may be substantially straight. That is, in FIG. 7, the outer tube 708 may be extended forward along the inner tube 710 thus straightening the inner tube 710 because the outer tube 708 may have a greater stiffness and less of a degree of curvature than the inner tube 710. Specifically, in FIG. 7 it can be seen that, if the outer tube attachment rod 734 is connected to the outer tube 708 but not the inner tube 710, translation of the outer tube attachment rod 734 within the slider channel 732 toward the back end 748 of the control mechanism 700 may cause refraction of the outer tube 708 relative to the inner tube 710. Thus, when this movement occurs, the inner tube 710 may be more exposed on the distal end of the scope, and thus uninhibited by the stiffness of the outer tube 708 allowing it to maintain its natural state of curvature. This movement may first require swiveling of the housing 704 relative to the scope attachment mechanism 706.

Figure 8:
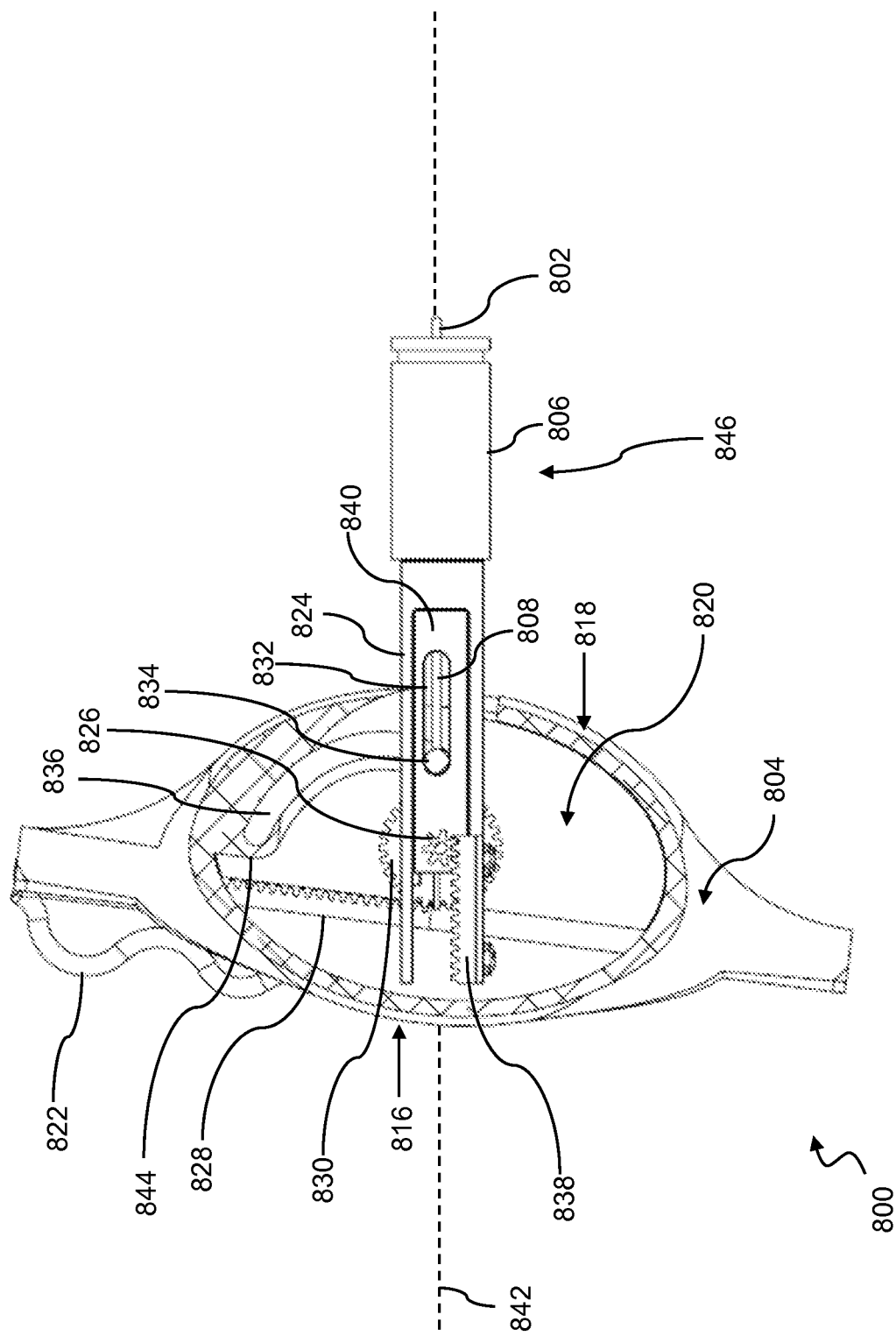
FIG. 8 is a cross-section of a control mechanism in a deployed, curved state.

FIG. 8 is a cross-section of a control mechanism in a deployed, curved state. In other words, in FIG. 8, the control mechanism 800 is positioned such that the nested tubes 802 are each translated forward relative to a scope, which may be a movement independent of translational movement of the scope. Also, in FIG. 8, the control mechanism 800 is positioned such that the outer tube 808 is retracted relative to the inner tube (the inner tube is not shown in FIG. 8). In an aspect, if the outer tube 808 has a greater stiffness and less of a degree of curvature than the inner tube, when the outer tube 808 is retracted relative to the inner tube, the inner tube is more exposed on the distal end of the scope and is thus uninhibited by the stiffness of the outer tube 808 allowing it to maintain its natural state of curvature. FIG. 8 shows a control mechanism 800, nested tubes 802, a housing 804, a scope attachment mechanism 806, a top portion 816, a bottom portion 818, a central portion 820, a finger interface 822, support rails 824, an axle 826, a tubing advancement slide rack 828, a tubing advancement gear 830, a slider channel 832, an outer tube attachment rod 834, a curvature adjustment channel 836, a support rail slide rack 838, and a tube attachment slider 840.

FIG. 8 may include a fully deployed, curved state for the control mechanism 800, where the finger interface 822 is displaced toward the scope attachment mechanism 806 a maximum length, where the housing 804 is swiveled relative to the scope attachment mechanism 806 a maximum length, and where the housing 804 is translated backward away from the scope attachment mechanism 806 along the axis 842.

As discussed above, displacing the finger interface 822 toward the scope attachment mechanism 806 may be caused by sliding the finger interface 822 along the slot on the top portion 816 of the housing 804 toward the front end 846 of the housing 804 as far as it may travel, i.e., until it reaches the end of the slot on the top portion 816 of the housing 804 on the front handle 812. When the finger interface 822 is slid forward toward the front end 846 of the housing 804, the tubing advancement slide rack 828 moves forward, which rotates the tubing advancement gear 830, which moves the axle 826 (and thus the housing 804) forward relative to the support rail slide rack 838. Thus, in an implementation, the finger interface 822 moves forward and thus advances the nested tubes 802.

The curvature of the nested tubes 802 may be controlled by adjusting the position of the outer tube 808 relative to the inner tube. In an embodiment, this is enabled by the outer tube attachment rod 834 because it is attached to the outer tube 808 but not the inner tube. Thus, translation of the outer tube attachment rod 834 translates the outer tube 808 relative to the inner tube. In an implementation, the outer tube attachment rod 834 is in a locked position when the housing 804 is not swiveled relative to the scope attachment mechanism 806 (i.e., when the housing 804 is longitudinally aligned with the scope attachment mechanism 806 as in FIGS. 5-7). The locking may be accomplished by a locking protrusion 844. However, when the housing 804 is swiveled, the locking protrusion 844 that is locking the outer tube attachment rod 834 is released (i.e., it moves upward relative to the outer tube attachment rod 834). Thus, the housing 804 may be pulled back by a user thereby sliding the outer tube attachment rod 834 backward along the slider channel 832. Because the outer tube attachment rod 834 is attached to the outer tube 808 in an embodiment, the sliding of the outer tube attachment rod 834 backward along the slider channel 832 also pulls the outer tube 808 backward, thereby retracting the outer tube 808 relative to the inner tube.

Therefore, to enable the curved state for the control mechanism 800, the housing 804 may first be swiveled relative to the scope attachment mechanism 806. This may be accomplished by a user manually swiveling the housing 804. The housing 804 may swivel about the axis of the axle 826, which attaches the housing 804 to the scope attachment mechanism 806 in an embodiment. When the housing 804 is swiveled, the outer tube attachment rod 834 may correspondingly move relative to the housing 804 along the central portion 820 of the housing 804 within the curvature adjustment channel 836. This motion may release the outer tube attachment rod 834 from a locking protrusion 844. Because the outer tube attachment rod 834 is attached to the outer tube 808 in an implementation, translational movement of the outer tube attachment rod 834 may cause either the advancement or retraction of the outer tube 808 relative to the inner tube 810, thus adjusting the curvature of the nested tubes 802. Thus, to enable the curved state for the control mechanism 800, after swiveling the housing 804 relative to the scope attachment mechanism 806, the housing 804 may be pulled back by a user thereby sliding the outer tube attachment rod 834 backward along the slider channel 832. Alternatively, the housing 804 may be pushed forward by a user thereby sliding the outer tube attachment rod 834 forward along the slider channel 832. Because the outer tube attachment rod 834 is attached to the outer tube 808 in an embodiment, the sliding of the outer tube attachment rod 834 backward or forward along the slider channel 832 pulls the outer tube 808 backward or pushes the outer tube 808 forward, respectively, thereby retracting or advancing the outer tube 808 relative to the inner tube. In FIG. 8, the outer tube 808 is fully retracted, and thus it is depicted as taking up the entire length of the slider channel 832.

Figure 9:
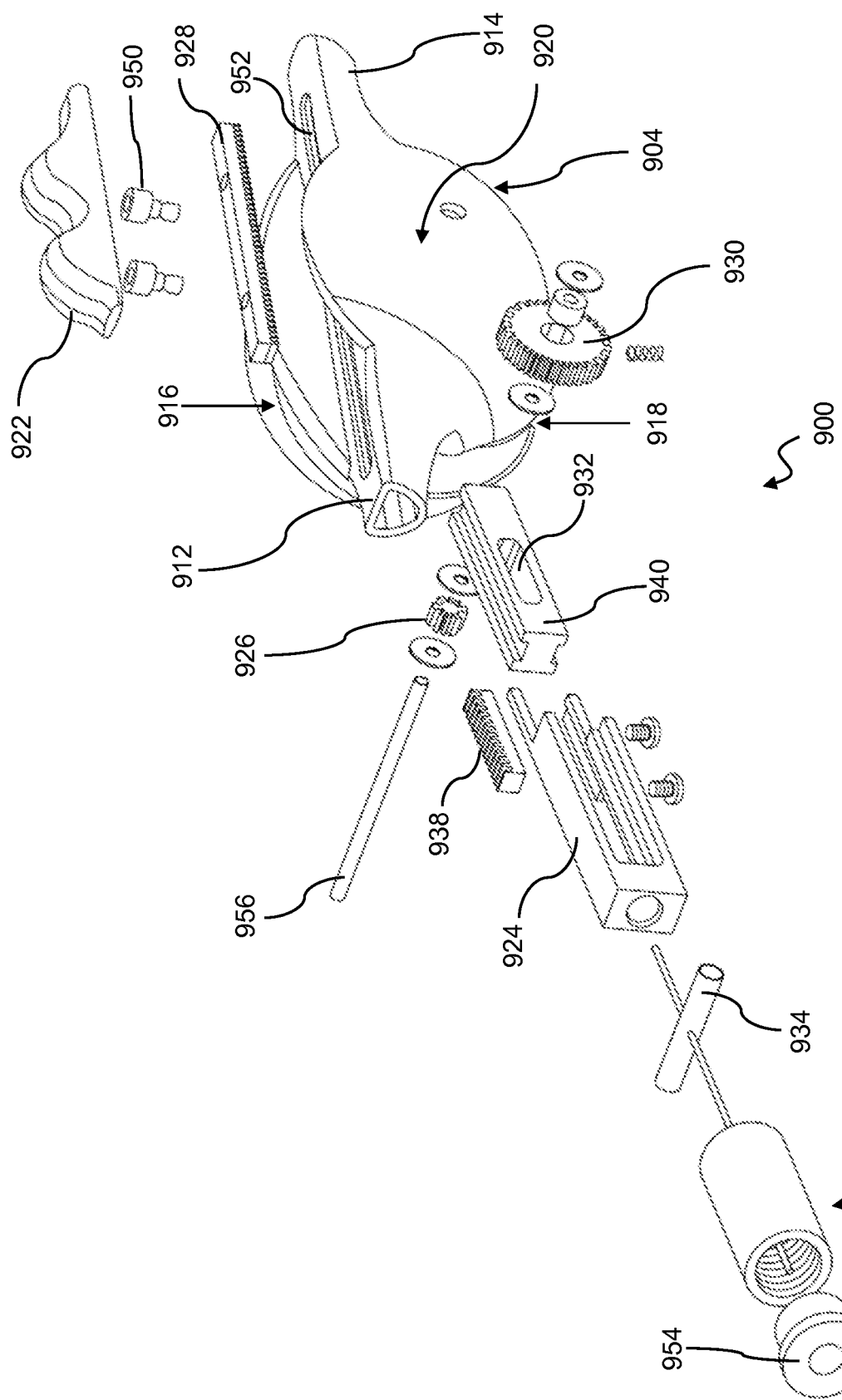
FIG. 9 is an exploded view of a control mechanism.

FIG. 9 is an exploded view of a control mechanism. As shown in FIG. 9, the control mechanism 900 may include a housing 904 and a scope attachment mechanism 906, with various mechanical components that enable control of nested tubes.

The housing 904 may include a front handle 912, a rear handle 914, a top portion 916, a bottom portion 918, and a central portion 920. The housing 904 may be configured to engage with a finger interface 922. The finger interface 922 may engage with a tubing advancement slide rack 928 via attachments 950. The top portion 916 of the housing 904 may include a slot 952 in which the finger interface 922 may slidably engage with the housing 904.

The scope attachment mechanism 906 may include an attachment interface 954 that is configured to attach to an endoscope handle or the like. The attachment interface 954 may also or instead be configured to attach the control mechanism 900 to the working channel of an endoscope.

The housing 904 may be configured to include mechanical components that enable control of nested tubes. These mechanical components may include support rails 924, an axle 926, a tubing advancement gear 930, a slider channel 932, an outer tube attachment rod 934, a support rail slide rack 938, and a tube attachment slider 940. The axle 926 and tubing advancement gear 930 may be configured to rotate about an axis via an axle rod 956.

FIG. 9 is provided to yield a better understanding of an embodiment of the control mechanism 900, but one of ordinary skill will understand that the various components shown in FIG. 9, or the other figures included herein for that matter, may be supplemented or replaced by other components, or in some instances omitted entirely. For example, FIG. 9 shows various attachment means (e.g., the attachments 950 for the finger interface 922 and tubing advancement slide rack 928, as well as other screws, washers, and the like depicted in FIG. 9), but a person of ordinary skill will recognize that other attachment means may be possible, including without limitation, bolts, clamps, clips, dowels, friction fits, snap fits, gibs, glue, hook and loop, latches, nails, nuts, pins, rivets, and so forth.

As stated above, the gearing of the aforementioned components may be adjusted as desired. Although the aforementioned components generally include gearing, teeth, slide racks, slots, rails, channels, and so forth, a person of ordinary skill will recognize that other means for cooperating these components may also or instead be possible. Furthermore, other mechanical configurations may be possible to provide the movements of the nested tubes that are desired, and all are intended to be included within the scope of this disclosure.

Figure 10:
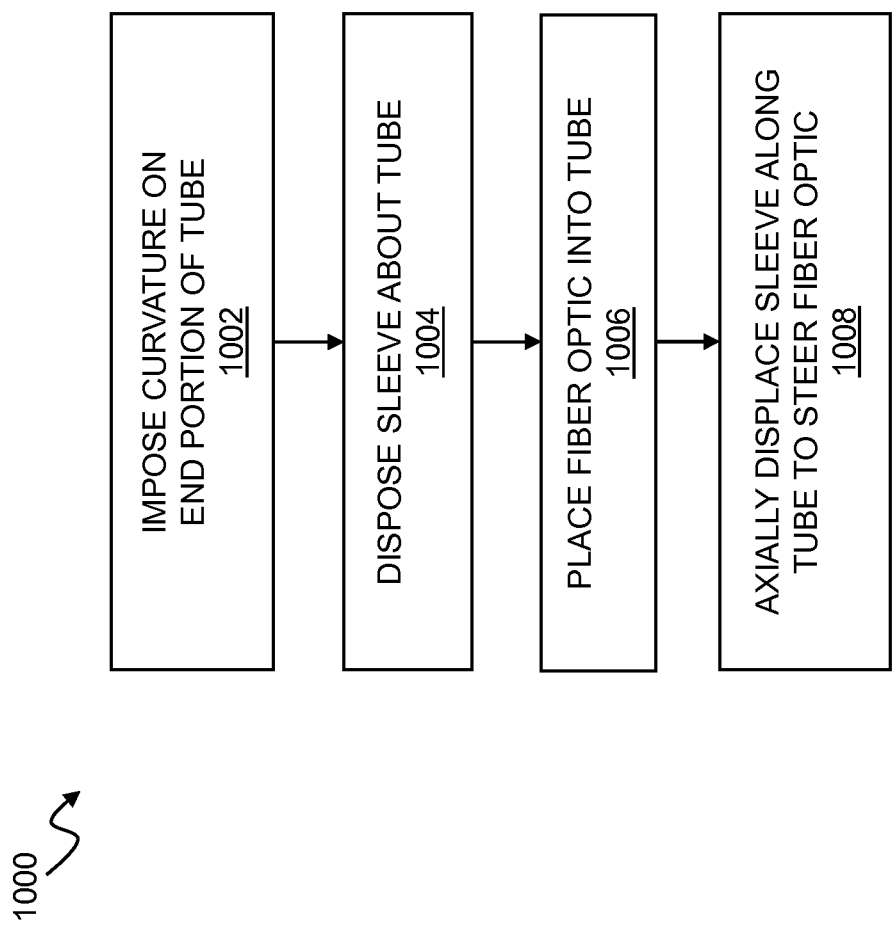
FIG. 10 is a flowchart of a method for steering an endoscopic tool.

FIG. 10 is a flowchart of a method for steering a scope apparatus.

As shown in step 1002, the method 1000 may include imposing a predetermined curvature on an end portion of a tube. The curvature may be imposed by a user using any suitable techniques for a particular material. As noted above, nitinol usefully provides a combination of high elasticity and suitable stiffness for the applications contemplated herein, and is amenable to shaping using known techniques. The tube may thus provide an end with a predetermined radius of curvature. The tube may also include a predetermined stiffness, which again may be based on the material of the tube. The tube may include a hollow core and an exit from the hollow core for a surgical tool. The surgical tool may include one or more of a laser fiber, a mini-scissor, a bipolar probe, and a drill.

As shown in step 1004, the method 1000 may include disposing a straight sleeve about the tube. The straight sleeve may have a greater stiffness than the end portion of the tube, at least in the area surrounding the end portion of the tube where steering occurs. The sleeve may be concentric with the tube, and have a terminal portion proximal to the end of the tube with a stiffness greater than the predetermined stiffness of the tube and a radius of curvature greater than the predetermined radius of curvature of the tube. The terminal portion of the sleeve may be straight. The sleeve may be formed of nitinol or the like.

The tube and the sleeve may include a casing that surrounds the tube and the sleeve, where the casing may form an endoscopic tool. The casing may include a remote end housing a second surgical tool proximal to the end of the tube, a control end distal to the end of the tube, and a channel for coupling the second surgical tool to the control end. The second surgical tool may include a camera, an illumination source, a cutting tool, and so forth. A control mechanism having a second control may axially rotate the tube within the casing, axially rotate the tube and the sleeve together within the casing, and so forth.

As shown in step 1006, the method 1000 may include placing a fiber optic with a tip into a hollow core of the tube so that the tip of the fiber optic extends beyond an end of the tube. A variety of useful tools and techniques may also be supported to augment surgical procedures as contemplated herein. For example, the method may further include supplying a fluid from a fluid source through the hollow core to the exit, e.g., for lens cleaning, irrigation, or the like.

As shown in step 1008, the method 1000 may include axially displacing the straight sleeve along the tube to steer the tip of the fiber optic. This may be accomplished by a control mechanism distal to the end of the tube with a control configured to change a curvature of the end of the tube by axially displacing the sleeve relative to the tube. The control mechanism may or instead include a second control configured to axially translate the end of the tube by uniformly axially displacing the tube and the sleeve. The control mechanism may also or instead include a third control configured to rotate the tube and the sleeve, or generally rotate the scope.

Figure 11:
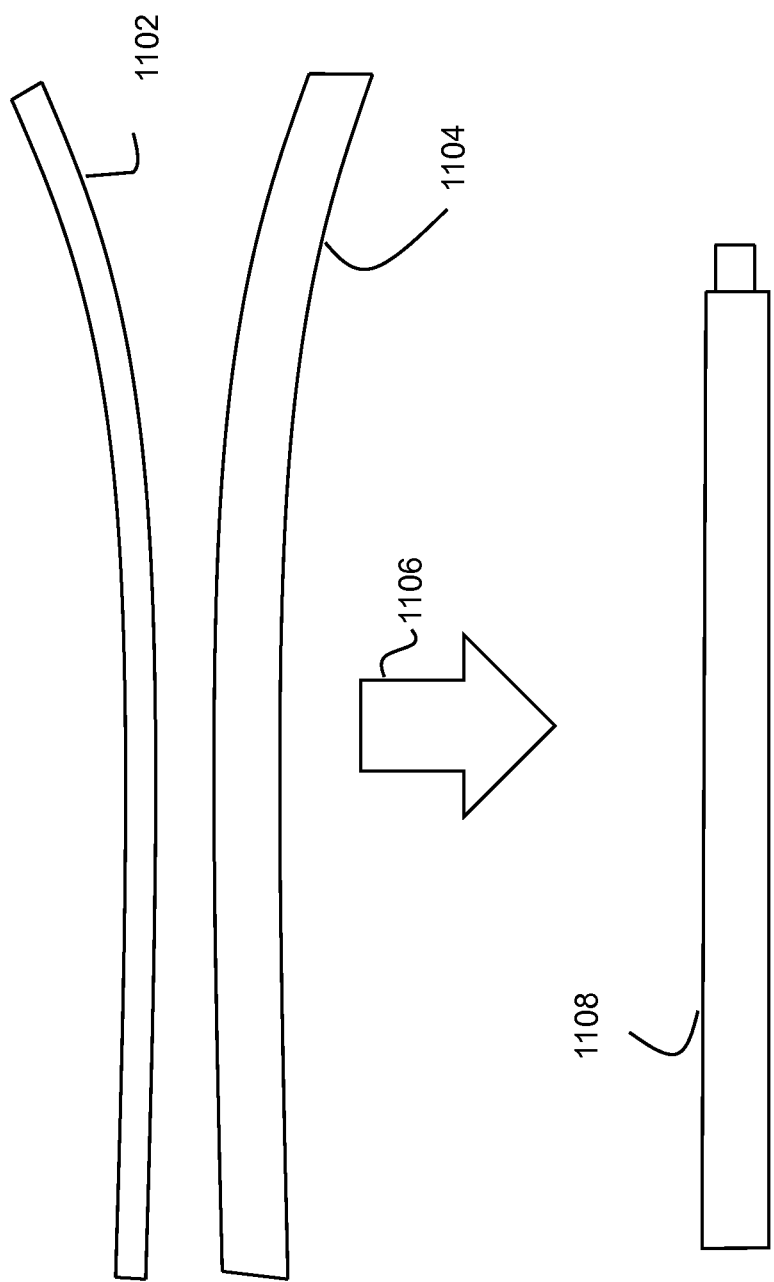
FIG. 11 shows a steerable tool using nested, curved sleeves.

FIG. 11 shows a steerable tool using nested, curved sleeves. As noted above, relative axial displacement of sleeves is one technique for tip steering. But tip steering may also or instead be controlled by axially rotating two concentric tubes relative to one another. By pre-biasing a curvature into two or more tubes or the like, various curvatures can be achieved. As shown in FIG. 11, a first tube 1102 may have a first curvature and a first stiffness, and a second tube 1104 may have a second curvature and a second stiffness. The two tubes may be combined by placing the first tube 1102 (having an outer diameter less than or equal to an inner diameter of the second tube 1104) inside the second tube 1104, as generally illustrated by an arrow 1106, resulting in a composite tube 1108.

By axially rotating the two tubes 1102, 1104 relative to one another, the composite tube 1108 may be rendered more straight (where curvatures are in opposition) or more curved (where curvatures are aligned). The curvatures and stiffness may optionally be selected so that when directly opposing one another, the composite tube 1108 is substantially straight, although this is not required for all steering applications. In another aspect, two or more rods or the like with various predetermined curvatures may be placed within a single tube for greater control over curvature.

Thus, in one aspect there is disclosed herein an apparatus including a first tube having a first end with a first predetermined radius of curvature and a first predetermined stiffness, the tube including a hollow core and an exit from the hollow core for a surgical tool, a second tube rotationally disposed within and concentric with the first tube, the second tube having a second end proximal to the first end with a second predetermined radius of curvature and a second predetermined stiffness, and a control mechanism distal to the first end of the first tube and the second end of the second tube with a control configured to change a curvature of the end of the tube by rotationally displacing the first tube relative to the second tube.

In another implementation, the concept of using concentric tubes for steering an endoscopic tool or the like may also or instead be applied to the entire distal end of the endoscope (i.e., to the endoscope itself) in addition to or in lieu of concentric tubes for steering a surgical tool traveling through the endoscope and exiting at the distal end thereof. In this implementation, the distal end of the endoscope itself may include a first tube having a first end with a first predetermined radius of curvature and a first predetermined stiffness, and a second tube rotationally disposed within and concentric with the first tube, where the second tube includes a second end proximal to the first end with a second predetermined radius of curvature and a second predetermined stiffness. A control mechanism, which may be the same control mechanism as that used for steering the surgical tool as described herein or a different control mechanism (e.g., the endoscopic handle), may be used to control these concentric tubes in a similar manner as described throughout this disclosure with regard to the concentric tubes housing the surgical tool.

In another aspect, any or all of the techniques described above may be applied to an endoscope or the like in order to control a curvature of a housing or body that is fed into a cavity. Among other things, this may facilitate centering of the endoscope (or other tool) within a cavity prior to steering or aiming an endoscopic tool deployed by the endoscope within the cavity.

In one aspect, the curvature of the concentric tubes, or the curvature of another portion of the steerable endoscopic tool, may be beneficial for particular uses, e.g., particular surgeries. For example, during spine surgery, the endoscope may be positioned with a particular curvature such that the endoscope hugs the dorsal wall of the spinal canal. This curvature may be applied before or during surgery through steering, or it may be a curvature that is provided by other means, e.g., manually applied to the endoscope before surgery. The curvature of the concentric tubes may be controlled to work in conjunction with the curvature of the endoscope to provide for ease of use in a particular application, e.g., to hug the dorsal wall of a spinal canal during spine surgery.

The above systems, devices, methods, processes, and the like may be tailored for use with an endoscope. For example, an embodiment includes a flexible endoscopic body having a first end and a second end, and a tube within the flexible endoscopic body having an end proximal to the first end of the flexible endoscopic body with a predetermined radius of curvature and a predetermined stiffness, where the tube includes a hollow core and an exit from the hollow core for a surgical tool. This embodiment may also include a sleeve slidably disposed outside of and concentric with the tube, where the sleeve has a terminal portion proximal to the end of the tube with a stiffness greater than the predetermined stiffness of the tube and a radius of curvature greater than the predetermined radius of curvature of the tube. This embodiment may also include a fiber optic within the hollow core extending from the first end to the second end of the flexible endoscopic body, a laser source coupled to the fiber optic and the second end of the flexible endoscopic body, and a control mechanism proximal to the second end of the flexible endoscopic body with a control configured to change a curvature of the end of the tube by axially displacing the sleeve relative to the tube. A camera and an illumination source may be housed in the first end of the flexible endoscopic body. A display may be coupled to the camera through a channel in the flexible endoscopic body.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. An apparatus comprising:
   a tube having an end with a predetermined radius of curvature and a predetermined stiffness, the tube including a hollow core and an exit from the hollow core at the end for a surgical tool;
   a laser fiber disposed in the hollow core as the surgical tool;
   a sleeve slidably disposed outside of and concentric with the tube, the sleeve having a terminal portion proximal to the end of the tube with a stiffness greater than the predetermined stiffness of the tube and a radius of curvature greater than the predetermined radius of curvature of the tube;
   an endoscopic body having a working channel around the tube and the sleeve; and
   a control mechanism coupled to the tube and sleeve through the working channel at a position along the endoscopic body distal to the end of the tube, the control mechanism configured for steering the end of the tube independently of the endoscopic body, the control mechanism including a housing with three controls comprising:
      a first control configured to axially displace the tube and the sleeve together to deploy the end of the tube from the endoscopic body in response to sliding a finger interface along a housing of the control mechanism without changing a curvature of the tube and the sleeve, wherein the finger interface is coupled to the tube and the sleeve through a mechanical configuration providing a change in mechanical advantage such that moving the finger interface on the control mechanism moves the end of the tube a small amount relative to a movement of the finger interface,
      a second control coupled to the tube and the sleeve and configured to rotate the tube and the sleeve within the endoscopic body in response to a rotation of the housing about a rotation axis of the housing to sweep a distal tip of the laser fiber within a surgical site when the apparatus is introduced to the surgical site for use, and
      a third control configured to change a curvature of the end of the tube by axially displacing the sleeve relative to the tube in response to swiveling the housing about a second axis of an axle within the housing the second axis different than the rotation axis.

2. The apparatus of claim 1 wherein the hollow core has a diameter of at least one millimeter.

3. The apparatus of claim 1 wherein the terminal portion of the sleeve is straight.

4. The apparatus of claim 1 wherein the end of the tube is formed of a shape memory alloy.

5. The apparatus of claim 4 wherein the end of the tube is formed of nitinol.

6. The apparatus of claim 1 wherein the terminal portion of the sleeve is formed of nitinol.

7. The apparatus of claim 1 wherein the first control is configured to axially translate the end by uniformly axially displacing the tube and the sleeve.

8. The apparatus of claim 1 wherein the endoscopic body includes:
  a remote end housing a second surgical tool proximal to the end of the tube;
  a control end distal to the end of the tube; and
  a channel for coupling the second surgical tool to the control end.

9. The apparatus of claim 8 wherein the second surgical tool includes a camera.

10. The apparatus of claim 1 wherein the second control is configured to axially rotate the tube within the endoscopic body.

11. The apparatus of claim 1 wherein the second control is configured to axially rotate the tube and the sleeve together within the endoscopic body.

12. The apparatus of claim 1 further comprising a source of a fluid.

13. The apparatus of claim 12 wherein the fluid is supplied from the source through the hollow core to the exit.

14. An endoscope comprising:
  a flexible endoscopic body having a first end and a second end;
  a tube within the flexible endoscopic body having an end proximal to the first end of the flexible endoscopic body with a predetermined radius of curvature and a predetermined stiffness, the tube including a hollow core and an exit from the hollow core for a surgical tool;
  a sleeve slidably disposed outside of and concentric with the tube, the sleeve having a terminal portion proximal to the end of the tube with a stiffness greater than the predetermined stiffness of the tube and a radius of curvature greater than the predetermined radius of curvature of the tube;
  a fiber optic within the hollow core extending from the first end to the second end of the flexible endoscopic body;
  a laser source coupled to the fiber optic and the second end of the flexible endoscopic body; and
  a control mechanism for controlling steering of the fiber optic independent of an endoscopic steering system for the flexible endoscopic body, the control mechanism coupled to the tube and sleeve through a working channel at a position along the flexible endoscopic body distal to the end of the tube, the control mechanism configured for steering the exit from end of the tube independently of an endoscope steering system for the endoscopic body, the control mechanism including a housing with three controls comprising:
    a first control configured to axially displace the tube and the sleeve together to deploy the end of the tube from the endoscopic body in response to sliding a finger interface along a housing of the control mechanism without changing a curvature of the tube and the sleeve, wherein the finger interface is coupled to the tube and the sleeve through a mechanical configuration providing a change in mechanical advantage such that moving the finger interface on the control mechanism moves the end of the tube a small amount relative to a movement of the finger interface,
    a second control coupled to the tube and the sleeve and configured to rotate one or more of the tube and the sleeve within the endoscopic body in response to a rotation of the housing about a rotation axis of the housing to sweep a distal tip of the fiber optic within a surgical site when the endoscope is introduced to the surgical site for use, and
    a third control configured to change a curvature of the end of the tube by axially displacing the sleeve relative to the tube in response to swiveling the housing about a second axis of an axle within the housing, the second axis different than the rotation axis.

15. The endoscope of claim 14 further comprising a camera housed in the first end of the flexible endoscopic body.

16. The apparatus of claim 1 wherein the first control enables the tube and sleeve to fully retract into the endoscopic body.

17. The apparatus of claim 1 wherein the first control includes a finger interface coupled to a tubing advancement slide rack, the tubing advancement slide rack further engaged with a tubing advancement gear rotatably coupled to the housing and coupled to a support rail slide rack engaged through the tubing advancement gear to cause translational movement of the housing relative to a scope attachment mechanism that couples the housing to the endoscopic body, thereby axially displacing the tube and the sleeve together within the endoscopic body.

18. The apparatus of claim 1 wherein the second control supports rotation of at least one of the tube and the sleeve about the rotation axis of the housing independent from a rotation of the endoscopic body.

19. The apparatus of claim 1 wherein the second axis is transverse to the rotation axis.

20. The apparatus of claim 1 wherein the third control includes an outer tube attachment rod coupled to the tube and controlling an axial position of the tube relative to the sleeve by sliding within a slider channel to a position at an intersection of a curvature adjustment channel in the housing and the slider channel, further wherein the curvature adjustment channel is shaped to displace the intersection axially along the slider channel as the housing rotates about the second axis.

21. The apparatus of claim 1 wherein the second control is configured to sweep the distal tip of the laser fiber within a field of view of the surgical site with a degree of rotational freedom independent from the endoscopic body.

* * * * *